United States Patent
Aoki et al.

(10) Patent No.: US 11,186,617 B2
(45) Date of Patent: Nov. 30, 2021

(54) EPITOPE

(71) Applicant: HOYU CO., LTD., Aichi (JP)

(72) Inventors: Yuji Aoki, Aichi (JP); Fumiaki Ono, Aichi (JP)

(73) Assignee: HOYU CO., LTD., Aichi (JP)

( * ) Notice: Subject to any disclaimer, the term of this patent is extended or adjusted under 35 U.S.C. 154(b) by 206 days.

(21) Appl. No.: 16/223,489

(22) Filed: Dec. 18, 2018

(65) Prior Publication Data

US 2019/0185525 A1   Jun. 20, 2019

(30) Foreign Application Priority Data

Dec. 19, 2017  (JP) ............................ JP2017-242849

(51) Int. Cl.
| | |
|---|---|
| C07K 14/415 | (2006.01) |
| G01N 33/576 | (2006.01) |
| A61P 37/08 | (2006.01) |
| G01N 33/52 | (2006.01) |
| G01N 33/574 | (2006.01) |
| A61K 39/35 | (2006.01) |
| G01N 33/68 | (2006.01) |
| A61K 38/00 | (2006.01) |

(52) U.S. Cl.
CPC ............ *C07K 14/415* (2013.01); *A61K 39/35* (2013.01); *A61P 37/08* (2018.01); *G01N 33/52* (2013.01); *G01N 33/5767* (2013.01); *G01N 33/57488* (2013.01); *G01N 33/6854* (2013.01); *A61K 38/00* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 10,053,497 B2 * | 8/2018 | Anderson | ............ C07K 14/415 |
| 2012/0167253 A1 | 6/2012 | Barro Losada et al. | |
| 2020/0393408 A1 | 12/2020 | Matsunaga et al. | |

FOREIGN PATENT DOCUMENTS

| | | |
|---|---|---|
| EP | 2064551 A2 | 6/2009 |
| JP | 2002-286716 A | 10/2002 |
| JP | 2005-198582 A | 7/2005 |
| JP | 2006-126083 A | 5/2006 |
| JP | 2011-033544 A | 2/2011 |
| JP | 2011-033546 A | 2/2011 |
| JP | 2011-033547 A | 2/2011 |
| JP | 2011-033548 A | 2/2011 |
| JP | 2012-510431 A | 5/2012 |
| JP | 2012-516680 A | 7/2012 |
| WO | 2010/060155 A1 | 6/2010 |
| WO | 2012/108827 A1 | 8/2012 |
| WO | WO-2012108827 A1 * | 8/2012 ............... A61P 31/22 |

OTHER PUBLICATIONS

Wachholz, Petra A., Rebecca J. Dearman, and Ian Kimber. "Detection of allergen-specific IgE antibody responses." Journal of immunotoxicology 1.3-4 (2005): 189-199. (Year: 2005).*

Albrecht, Melanie, et al. "Relevance of IgE binding to short peptides for the allergenic activity of food allergens." Journal of Allergy and Clinical Immunology 124.2 (2009): 328-336. (Year: 2009).*

Palosuo, Kati, et al. "Wheat ω-5 gliadin is a major allergen in children with immediate allergy to ingested wheat." Journal of allergy and clinical immunology 108.4 (2001): 634-638. (Year: 2001).*

Colman, Peter M. "Effects of amino acid sequence changes on antibody-antigen interactions." Research in Immunology 145.1 (1994): 33-36. (Year: 1994).*

Lubert Stryer, Biochemistry, 4th, WH Freeman, New York (1995) ISBN: 0-7167-2009-4 (Year: 1995).*

Fields, Gregg B. "Introduction to peptide synthesis." Current protocols in protein science vol. Chapter 18 (2002): Unit 18.1. doi: 10.1002/0471140864.ps1801s26 (Year: 2002).*

Battais et al., Identification of IgE-binding epitopes on gliadins for patients with food allergy tok wheat. Allergy. 2005;60:815-821.

RayBiotech, Peptide Array-Based Epitope Mapping Services. funakoshi. Retrieved online at: https://www.funakoshi.co.ip/contents/65252. 6 pages, Sep. 15, 2016.

SIGMA, GENOSYS, PEPscreen, The first step to peptide drug discovery research. Retrieved online at: https://www.sigmaaldrich.com/content/dam/sigma-aldrich/doc/SAJ/Brochure/1/j_pepsc/lowres.pdf. 14 pages, Feb. 1, 2008.

Battias et al., Identification of IgE-binding epitopes on gliadins for patients with food allergy to wheat. Allergy. 2005;60:815-821.

Bouchez-Mahiout et al., Low molecular weight glutenins in wheat-dependant, exercise-induced anaphylaxis: allergenicity and antigenic relationships with omega 5-gliadins. Int Arch Allergy Immunol. 2010;153(1):35-45.

(Continued)

*Primary Examiner* — Michael Szperka
*Assistant Examiner* — Lia E Taylor
(74) *Attorney, Agent, or Firm* — McCarter & English, LLP; Yu Lu

(57) ABSTRACT

The present invention relates to a polypeptide comprising an epitope of an antigen; a kit and a composition for diagnosing allergy, wherein the kit and the composition comprise the aforementioned polypeptide, and a method for diagnosing allergy and a method for treating allergy, wherein the methods use the aforementioned polypeptide; a pharmaceutical composition comprising the aforementioned polypeptide; and a raw material or a processed product in which the antigen comprising the aforementioned polypeptide is removed or reduced. Furthermore, the present invention relates to a tester for determining the presence or absence of the antigen in an object.

9 Claims, 3 Drawing Sheets
Specification includes a Sequence Listing.

(56) References Cited

OTHER PUBLICATIONS

Du et al., Molecular characterization of the IgE-binding epitopes in the fast omega-gliadins of Triticeae in relation to wheat-dependent, exercise-induced anaphylaxis. Gene. Oct. 10, 2016;591(1):27-33.

Juhasz et al., The epitopes in wheat proteins for defining toxic units relevant to human health. Funct Integr Genomics. Nov. 2012;12(4):585-98.

Raybiotech, Peptide Array-Based Epitope Mapping Service. funakoshi. Retrieved online at: https://www.funakoshi.co.ip/contents/65252. 6 pages, Sep. 15, 2016.

SIGMA, GENOSYS, PEPscreen, The first step to peptide drug discovery research. Retrieved online at: https://www.sigmaaldrich.com/content/dam/sigma-aldrich/docs/SAJ/Brochure/1/j_pepsc_lowres.pdf. 14 pages, Feb. 1, 2008.

Partial European Search Report for Application No. 18213848.7, dated May 9, 2019, 24 pages.

Matsuo et al., Identification of the IgE-binding epitope in omega-5 gliadin, a major allergen in wheat-dependent exercise-induced anaphylaxis. J Biol Chem. Mar. 26, 2004;279(13):12135-40.

Matsuo et al., Molecular cloning, recombinant expression and IgE-binding epitope of omega-5 gliadin, a major allergen in wheat-dependent exercise-induced anaphylaxis. FEBS J. Sep. 2005;272(17):4431-8.

Bruins Slot et al., Immunochemical Detection Methods for Gluten in Food Products: Where Do We Go from Here? Crit Rev Food Sci Nutr. Nov. 17, 2016;56(15):2455-2466.

Lee et al., Comprehensive identification of LMW-GS genes and their protein products in a common wheat variety. Funct Integr Genomics. May 2016;16(3):269-79, Supplemental Materials.

Leszczynska et al., The Usefulness of Rabbit Anti-QQQPP Peptide Antibodies to Wheat Flour Antigenicity Studies. Czech J Food Sci. 2008;26(1):24-30.

Matsuo et al., Common food allergens and their IgE-binding epitopes. Allergol Int. Oct. 2015;64(4):332-43.

UniProt Accession No. B2BZD1, 4 pages, May 20, 2008.

Partial European Search Report for Application No. 20179456.7, dated Nov. 9, 2020, 21 pages.

U.S. Appl. No. 16/899,643, filed Jun. 12, 2020, 2020-0393408, Published.

Escudero et al., Characterization of peptides released by in vitro digestion of pork meat. J Agric Food Chem. Apr. 28, 2010;58(8):5160-5.

\* cited by examiner

Fig. 1

SPOT No.1

P1  P2  P3  N1  N2

QQFPQQEFPQQQQFP (SEQ ID NO: 6)

SPOT NO.2

P1  P2  P3  N1  N2

PQQQPPQQHQFPQQQ (SEQ ID NO: 13)

SEQUENCE LISTING

```
<160> NUMBER OF SEQ ID NOS: 52

<210> SEQ ID NO 1
<211> LENGTH: 7
<212> TYPE: PRT
<213> ORGANISM: Artificial Sequence
<220> FEATURE:
<223> OTHER INFORMATION: epitope
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
```

```
<222> LOCATION: (5)..(6)
<223> OTHER INFORMATION: Xaa can be any amino acid

<400> SEQUENCE: 1

Xaa Glu Xaa Pro Xaa Xaa Gln
1               5

<210> SEQ ID NO 2
<211> LENGTH: 7
<212> TYPE: PRT
<213> ORGANISM: Artificial Sequence
<220> FEATURE:
<223> OTHER INFORMATION: epitope
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (5)..(6)
<223> OTHER INFORMATION: Xaa can be any amino acid

<400> SEQUENCE: 2

Gln Glu Xaa Pro Xaa Xaa Gln
1               5

<210> SEQ ID NO 3
<211> LENGTH: 7
<212> TYPE: PRT
<213> ORGANISM: Artificial Sequence
<220> FEATURE:
<223> OTHER INFORMATION: epitope
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid

<400> SEQUENCE: 3

Gln Glu Xaa Pro Xaa Gln Gln
1               5

<210> SEQ ID NO 4
<211> LENGTH: 8
<212> TYPE: PRT
<213> ORGANISM: Artificial Sequence
<220> FEATURE:
<223> OTHER INFORMATION: epitope
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (6)..(7)
<223> OTHER INFORMATION: Xaa can be any amino acid

<400> SEQUENCE: 4

Gln Xaa Glu Xaa Pro Xaa Xaa Gln
1               5

<210> SEQ ID NO 5
<211> LENGTH: 10
<212> TYPE: PRT
```

```
<213> ORGANISM: Artificial Sequence
<220> FEATURE:
<223> OTHER INFORMATION: epitope
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (6)..(6)
<223> OTHER INFORMATION: Xaa can be any amino acid
<220> FEATURE:
<221> NAME/KEY: misc_feature
<222> LOCATION: (8)..(9)
<223> OTHER INFORMATION: Xaa can be any amino acid

<400> SEQUENCE: 5

Phe Pro Gln Xaa Glu Xaa Pro Xaa Xaa Gln
1               5                   10

<210> SEQ ID NO 6
<211> LENGTH: 15
<212> TYPE: PRT
<213> ORGANISM: Artificial Sequence
<220> FEATURE:
<223> OTHER INFORMATION: epitope

<400> SEQUENCE: 6

Gln Gln Phe Pro Gln Gln Glu Phe Pro Gln Gln Gln Gln Phe Pro
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: epitope

<400> SEQUENCE: 7

Gln Gln Phe Pro Gln Gln Glu Ala Pro Gln Gln Gln Gln Phe Pro
1               5                   10                  15

<210> SEQ ID NO 8
<211> LENGTH: 8
<212> TYPE: PRT
<213> ORGANISM: Artificial Sequence
<220> FEATURE:
<223> OTHER INFORMATION: epitope
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (4)..(5)
<223> OTHER INFORMATION: Xaa can be any amino acid

<400> SEQUENCE: 8

Pro Xaa Gln Xaa Xaa Pro Gln Gln
1               5

<210> SEQ ID NO 9
<211> LENGTH: 8
<212> TYPE: PRT
<213> ORGANISM: Artificial Sequence
<220> FEATURE:
<223> OTHER INFORMATION: epitope
<220> FEATURE:
<221> NAME/KEY: misc_feature
<222> LOCATION: (4)..(5)
<223> OTHER INFORMATION: Xaa can be any amino acid
```

<400> SEQUENCE: 9

Pro Gln Gln Xaa Xaa Pro Gln Gln
1               5

<210> SEQ ID NO 10
<211> LENGTH: 9
<212> TYPE: PRT
<213> ORGANISM: Artificial Sequence
<220> FEATURE:
<223> OTHER INFORMATION: epitope
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (5)..(6)
<223> OTHER INFORMATION: Xaa can be any amino acid

<400> SEQUENCE: 10

Phe Pro Xaa Gln Xaa Xaa Pro Gln Gln
1               5

<210> SEQ ID NO 11
<211> LENGTH: 9
<212> TYPE: PRT
<213> ORGANISM: Artificial Sequence
<220> FEATURE:
<223> OTHER INFORMATION: epitope
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (4)..(5)
<223> OTHER INFORMATION: Xaa can be any amino acid

<400> SEQUENCE: 11

Pro Xaa Gln Xaa Xaa Pro Gln Gln His
1               5

<210> SEQ ID NO 12
<211> LENGTH: 10
<212> TYPE: PRT
<213> ORGANISM: Artificial Sequence
<220> FEATURE:
<223> OTHER INFORMATION: epitope
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (5)..(6)
<223> OTHER INFORMATION: Xaa can be any amino acid

<400> SEQUENCE: 12

Phe Pro Xaa Gln Xaa Xaa Pro Gln Gln His
1               5                   10

<210> SEQ ID NO 13
<211> LENGTH: 15
<212> TYPE: PRT
<213> ORGANISM: Artificial Sequence
<220> FEATURE:
<223> OTHER INFORMATION: epitope

<400> SEQUENCE: 13

Pro Gln Gln Gln Pro Pro Gln Gln His Gln Phe Pro Gln Gln Gln
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: epitope

<400> SEQUENCE: 14

Pro Gln Gln Gln Ala Pro Gln Gln His Gln Phe Pro Gln Gln Gln
1               5                   10                  15

<210> SEQ ID NO 15
<211> LENGTH: 25
<212> TYPE: PRT
<213> ORGANISM: Artificial Sequence
<220> FEATURE:
<223> OTHER INFORMATION: epitope candidate

<400> SEQUENCE: 15

Gln Phe Pro Gln Gln Gln Phe Pro Gln Gln Glu Phe Pro Gln Gln
1               5                   10                  15

Gln Phe Pro Gln Gln Gln Ile Ala Arg
            20                  25

<210> SEQ ID NO 16
<211> LENGTH: 10
<212> TYPE: PRT
<213> ORGANISM: Artificial Sequence
<220> FEATURE:
<223> OTHER INFORMATION: epitope candidate

<400> SEQUENCE: 16

Glu Phe Pro Gln Gln Gln Gln Phe Pro Gln
1               5                   10

<210> SEQ ID NO 17
<211> LENGTH: 10
<212> TYPE: PRT
<213> ORGANISM: Artificial Sequence
<220> FEATURE:
<223> OTHER INFORMATION: epitope candidate

<400> SEQUENCE: 17

Gln Glu Phe Pro Gln Gln Gln Gln Phe Pro
1               5                   10

<210> SEQ ID NO 18
<211> LENGTH: 10
<212> TYPE: PRT
<213> ORGANISM: Artificial Sequence
<220> FEATURE:
<223> OTHER INFORMATION: epitope candidate

<400> SEQUENCE: 18

Gln Gln Glu Phe Pro Gln Gln Gln Gln Phe
1               5                   10

<210> SEQ ID NO 19
<211> LENGTH: 10
<212> TYPE: PRT
<213> ORGANISM: Artificial Sequence
<220> FEATURE:
<223> OTHER INFORMATION: epitope candidate

```
<400> SEQUENCE: 19

Pro Gln Gln Glu Phe Pro Gln Gln Gln
1               5                   10

<210> SEQ ID NO 20
<211> LENGTH: 10
<212> TYPE: PRT
<213> ORGANISM: Artificial Sequence
<220> FEATURE:
<223> OTHER INFORMATION: epitope candidate

<400> SEQUENCE: 20

Phe Pro Gln Gln Glu Phe Pro Gln Gln Gln
1               5                   10

<210> SEQ ID NO 21
<211> LENGTH: 10
<212> TYPE: PRT
<213> ORGANISM: Artificial Sequence
<220> FEATURE:
<223> OTHER INFORMATION: epitope candidate

<400> SEQUENCE: 21

Gln Phe Pro Gln Gln Glu Phe Pro Gln Gln
1               5                   10

<210> SEQ ID NO 22
<211> LENGTH: 7
<212> TYPE: PRT
<213> ORGANISM: Artificial Sequence
<220> FEATURE:
<223> OTHER INFORMATION: epitope

<400> SEQUENCE: 22

Gln Glu Phe Pro Gln Gln Gln
1               5

<210> SEQ ID NO 23
<211> LENGTH: 24
<212> TYPE: PRT
<213> ORGANISM: Artificial Sequence
<220> FEATURE:
<223> OTHER INFORMATION: epitope candidate

<400> SEQUENCE: 23

Gln Phe Leu Gln Gln Gln Phe Pro Gln Gln Pro Pro Gln Gln
1               5                   10                  15

His Gln Phe Pro Gln Gln Gln Leu
            20

<210> SEQ ID NO 24
<211> LENGTH: 10
<212> TYPE: PRT
<213> ORGANISM: Artificial Sequence
<220> FEATURE:
<223> OTHER INFORMATION: epitope candidate

<400> SEQUENCE: 24

Gln Gln Gln Pro Pro Gln Gln His Gln Phe
1               5                   10

<210> SEQ ID NO 25
<211> LENGTH: 10
<212> TYPE: PRT
<213> ORGANISM: Artificial Sequence
<220> FEATURE:
```

<223> OTHER INFORMATION: epitope candidate

<400> SEQUENCE: 25

Pro Gln Gln Gln Pro Pro Gln Gln His Gln
1               5                   10

<210> SEQ ID NO 26
<211> LENGTH: 10
<212> TYPE: PRT
<213> ORGANISM: Artificial Sequence
<220> FEATURE:
<223> OTHER INFORMATION: epitope candidate

<400> SEQUENCE: 26

Phe Pro Gln Gln Gln Pro Pro Gln Gln His
1               5                   10

<210> SEQ ID NO 27
<211> LENGTH: 10
<212> TYPE: PRT
<213> ORGANISM: Artificial Sequence
<220> FEATURE:
<223> OTHER INFORMATION: epitope candidate

<400> SEQUENCE: 27

Gln Phe Pro Gln Gln Gln Pro Pro Gln Gln
1               5                   10

<210> SEQ ID NO 28
<211> LENGTH: 10
<212> TYPE: PRT
<213> ORGANISM: Artificial Sequence
<220> FEATURE:
<223> OTHER INFORMATION: epitope candidate

<400> SEQUENCE: 28

Gln Gln Phe Pro Gln Gln Gln Pro Pro Gln
1               5                   10

<210> SEQ ID NO 29
<211> LENGTH: 8
<212> TYPE: PRT
<213> ORGANISM: Artificial Sequence
<220> FEATURE:
<223> OTHER INFORMATION: epitope

<400> SEQUENCE: 29

Pro Gln Gln Gln Pro Pro Gln Gln
1               5

<210> SEQ ID NO 30
<211> LENGTH: 15
<212> TYPE: PRT
<213> ORGANISM: Artificial Sequence
<220> FEATURE:
<223> OTHER INFORMATION: modified epitope

<400> SEQUENCE: 30

Gln Gln Phe Pro Gln Gln Glu Phe Pro Gln Gln Ala Gln Phe Pro
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: modified epitope

<400> SEQUENCE: 31

Gln Gln Phe Pro Gln Gln Glu Phe Pro Gln Ala Gln Gln Phe Pro
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: modified epitope

<400> SEQUENCE: 32

Gln Gln Phe Pro Gln Gln Glu Phe Pro Ala Gln Gln Gln Phe Pro
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: modified epitope

<400> SEQUENCE: 33

Gln Gln Phe Pro Gln Gln Glu Phe Ala Gln Gln Gln Gln Phe Pro
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: modified epitope

<400> SEQUENCE: 34

Gln Gln Phe Pro Gln Gln Ala Phe Pro Gln Gln Gln Gln Phe Pro
1 5 10 15

<210> SEQ ID NO 35
<211> LENGTH: 15
<212> TYPE: PRT
<213> ORGANISM: Artificial Sequence
<220> FEATURE:
<223> OTHER INFORMATION: modified epitope

<400> SEQUENCE: 35

Gln Gln Phe Pro Gln Ala Glu Phe Pro Gln Gln Gln Gln Phe Pro
1 5 10 15

<210> SEQ ID NO 36
<211> LENGTH: 15
<212> TYPE: PRT
<213> ORGANISM: Artificial Sequence
<220> FEATURE:
<223> OTHER INFORMATION: modified epitope

<400> SEQUENCE: 36

Pro Gln Gln Gln Pro Pro Gln Ala His Gln Phe Pro Gln Gln Gln
1 5 10 15

<210> SEQ ID NO 37
<211> LENGTH: 15
<212> TYPE: PRT
<213> ORGANISM: Artificial Sequence
<220> FEATURE:
<223> OTHER INFORMATION: modified epitope -continued

```
<400> SEQUENCE: 37

Pro Gln Gln Gln Pro Ala Gln His Gln Phe Pro Gln Gln Gln
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: modified epitope

<400> SEQUENCE: 38

Pro Gln Gln Gln Pro Ala Gln Gln His Gln Phe Pro Gln Gln Gln
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: modified epitope

<400> SEQUENCE: 39

Pro Gln Gln Ala Pro Pro Gln Gln His Gln Phe Pro Gln Gln Gln
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: modified epitope

<400> SEQUENCE: 40

Pro Gln Ala Gln Pro Pro Gln Gln His Gln Phe Pro Gln Gln Gln
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: modified epitope

<400> SEQUENCE: 41

Pro Ala Gln Gln Pro Pro Gln Gln His Gln Phe Pro Gln Gln Gln
1               5                   10                  15

<210> SEQ ID NO 42
<211> LENGTH: 15
<212> TYPE: PRT
<213> ORGANISM: Artificial Sequnece
<220> FEATURE:
<223> OTHER INFORMATION: modified epitope

<400> SEQUENCE: 42

Ala Gln Gln Gln Pro Pro Gln Gln His Gln Phe Pro Gln Gln Gln
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: known epitope

<400> SEQUENCE: 43
```

Gln Gln Ile Pro Gln Gln Gln
1               5

<210> SEQ ID NO 44
<211> LENGTH: 7
<212> TYPE: PRT
<213> ORGANISM: Artificial Sequence
<220> FEATURE:
<223> OTHER INFORMATION: known epitope

<400> SEQUENCE: 44

Gln Gln Leu Pro Gln Gln Gln
1               5

<210> SEQ ID NO 45
<211> LENGTH: 7
<212> TYPE: PRT
<213> ORGANISM: Artificial Sequence
<220> FEATURE:
<223> OTHER INFORMATION: known epitope

<400> SEQUENCE: 45

Gln Gln Phe Pro Gln Gln Gln
1               5

<210> SEQ ID NO 46
<211> LENGTH: 8
<212> TYPE: PRT
<213> ORGANISM: Artificial Sequence
<220> FEATURE:
<223> OTHER INFORMATION: epitope

<400> SEQUENCE: 46

Gln Gln Glu Phe Pro Gln Gln Gln
1               5

<210> SEQ ID NO 47
<211> LENGTH: 10
<212> TYPE: PRT
<213> ORGANISM: Artificial Sequence
<220> FEATURE:
<223> OTHER INFORMATION: epitope

<400> SEQUENCE: 47

Phe Pro Gln Gln Glu Phe Pro Gln Gln Gln
1               5                   10

<210> SEQ ID NO 48
<211> LENGTH: 9
<212> TYPE: PRT
<213> ORGANISM: Artificial Sequence
<220> FEATURE:
<223> OTHER INFORMATION: epitope

<400> SEQUENCE: 48

Phe Pro Gln Gln Gln Pro Pro Gln Gln
1               5

<210> SEQ ID NO 49
<211> LENGTH: 9
<212> TYPE: PRT
<213> ORGANISM: Artificial Sequence
<220> FEATURE:
<223> OTHER INFORMATION: epitope

<400> SEQUENCE: 49

```
Pro Gln Gln Gln Pro Pro Gln Gln His
1               5
```

<210> SEQ ID NO 50
<211> LENGTH: 10
<212> TYPE: PRT
<213> ORGANISM: Artificial Sequence
<220> FEATURE:
<223> OTHER INFORMATION: epitope

<400> SEQUENCE: 50

```
Phe Pro Gln Gln Gln Pro Pro Gln Gln His
1               5                   10
```

<210> SEQ ID NO 51
<211> LENGTH: 439
<212> TYPE: PRT
<213> ORGANISM: Triticum aestivum

<400> SEQUENCE: 51

```
Met Lys Thr Phe Ile Ile Phe Val Leu Leu Ala Met Ala Met Asn Ile
1               5                   10                  15

Ala Ser Ala Ser Arg Leu Leu Ser Pro Arg Gly Lys Glu Leu His Thr
            20                  25                  30

Pro Gln Glu Gln Phe Pro Gln Gln Gln Phe Pro Gln Pro Gln Gln
        35                  40                  45

Phe Pro Gln Gln Ile Pro Gln Gln His Gln Ile Pro Gln Gln Pro
    50                  55                  60

Gln Gln Phe Pro Gln Gln Gln Phe Leu Gln Gln Gln Ile Pro
65                  70                  75                  80

Gln Gln Ile Pro Gln Gln His Gln Ile Pro Gln Gln Pro Gln Gln
                85                  90                  95

Phe Pro Gln Gln Gln Phe Pro Gln Gln His Gln Ser Pro Gln Gln
            100                 105                 110

Gln Phe Pro Gln Gln Gln Phe Pro Gln Gln Lys Leu Pro Gln Gln Glu
    115                 120                 125

Phe Pro Gln Gln Gln Ile Ser Gln Gln Pro Gln Gln Leu Pro Gln Gln
130                 135                 140

Gln Gln Ile Pro Gln Gln Pro Gln Gln Phe Leu Gln Gln Gln Phe
145                 150                 155                 160

Pro Gln Gln Gln Pro Pro Gln Gln His Gln Phe Pro Gln Gln Gln Leu
            165                 170                 175

Pro Gln Gln Gln Gln Ile Pro Gln Gln Gln Ile Pro Gln Gln Pro
            180                 185                 190

Gln Gln Ile Pro Gln Gln Gln Ile Pro Gln Gln Pro Gln Gln Phe
        195                 200                 205

Pro Gln Gln Gln Phe Pro Gln Gln Gln Phe Pro Gln Gln Gln Phe Pro
210                 215                 220

Gln Gln Glu Phe Pro Gln Gln Gln Phe Pro Gln Gln Gln Ile Ala
225                 230                 235                 240

Arg Gln Pro Gln Gln Leu Pro Gln Gln Gln Ile Pro Gln Gln Pro
            245                 250                 255

Gln Gln Phe Pro Gln Gln Gln Phe Pro Gln Gln Gln Ser Pro Gln
            260                 265                 270

Gln Gln Gln Phe Pro Gln Gln Gln Phe Pro Gln Gln Gln Leu Pro
        275                 280                 285

Gln Lys Gln Phe Pro Gln Pro Gln Gln Ile Pro Gln Gln Gln Ile
```

```
                290               295               300
Pro Gln Gln Pro Gln Gln Phe Pro Gln Gln Gln Phe Pro Gln Gln
305                 310               315               320

Gln Phe Pro Gln Gln Gln Glu Phe Pro Gln Gln Phe Pro Gln Gln
                325               330               335

Gln Phe His Gln Gln Leu Pro Gln Gln Phe Pro Gln Gln
            340               345               350

Phe Pro Gln Gln Gln Phe Pro Gln Gln Gln Phe Pro Gln Gln Gln
        355               360               365

Gln Leu Thr Gln Gln Gln Phe Pro Arg Pro Gln Gln Ser Pro Glu Gln
    370               375               380

Gln Gln Phe Pro Gln Gln Gln Phe Pro Gln Gln Pro Pro Gln Gln Phe
385               390               395               400

Pro Gln Gln Gln Phe Pro Ile Pro Tyr Pro Pro Gln Gln Ser Glu Glu
            405               410               415

Pro Ser Pro Tyr Gln Gln Tyr Pro Gln Gln Pro Ser Gly Ser Asp
        420               425               430

Val Ile Ser Ile Ser Gly Leu
        435

<210> SEQ ID NO 52
<211> LENGTH: 1320
<212> TYPE: DNA
<213> ORGANISM: Triticum aestivum

<400> SEQUENCE: 52
atgaagacct tcatcatatt tgtcctcctt gccatggcga tgaacatcgc cagtgccagt      60
aggctgctaa gccctagagg caaggaattg catactccac aagaacaatt cccccaacaa     120
caacaattcc cccaaccaca acaattcccc caacaacaaa tccccccaaca acatcaaatc    180 ccccagcaac acaacaatt ccccccaacaa caacaattcc tccaacaaca caaatcccg      240 caacaacaaa tccccccaaca acatcaaatc ccccagcaac acaacaatt ccccagcaa      300 cagcaattcc cccaacaaca ccatccccc caacaacaat tcccacaaca caattcccc      360 caacagaaat tgccgcaaca ggaattccca caacaacaaa tctcccagca ccacaacaa      420 ctcccccagc aacaacaaat ccccccagcaa ccacaacaat ttctccaaca caacaattc     480 ccccagcaac aaccccccca acaacatcaa tttccccaac agcaattgcc ccaacaacaa     540
caaatccccc aacaacaaca gatccccccag caaccacaac aaatccccca acaacaacaa    600 atccccccagc aaccacaaca attcccccaa caacaattcc cgcaacaaca atttccccaa    660
cagcaattcc cgcaacagga attcccacaa caacaacaat tcccgcaaca acaaatcgcc    720
cggcaaccac aacaactccc ccaacaacaa caaatccccc agcaaccaca caatttcccc    780
caacaacaac aattccccca gcaacaatca ccccaacaac agcaatttcc ccaacaacaa    840 ttccccccaac aacaacaatt accgcaaaaa caattccccc aaccacaaca aatacccccaa    900 caacaacaaa tccccagca ccacaacaa ttccccagc aacaattccc ccaacaacag          960
caatttcccc aacaacaaga attcccccaa cagcaattcc cgcaacaaca attccaccaa     1020
caacaattac cgcaacaaca atttcccaa caacaattcc cccaacagca attccccaa       1080 caacaacagt tccccaaca acaacaatta acgcaacaac aattccccg ccacaacaa        1140 tcccctgaac aacaacaatt cccccaacaa caattccccc agcaaccacc acaacaattc     1200
```

```
cccaacaac aatttccaat accataccca ccccagcaat cagaagaacc ttccccatac    1260
caacaatatc cacaacaaca accatctggg agcgacgtta taagtatcag tggcctatga   1320
```

EPITOPE

CROSS-REFERENCE TO RELATED APPLICATIONS

This application claims the benefit of Japanese Patent Application No. 2017-242849, filed on Dec. 19, 2017. The entire contents of the aforementioned application are incorporated herein by reference.

TECHNICAL FIELD

The present invention relates to a polypeptide comprising an epitope of an antigen. The present invention also relates to a kit and a composition for diagnosing allergy, wherein the kit and the composition comprise the aforementioned polypeptide, and a method for diagnosing allergy and a method for treating allergy, wherein the methods use the aforementioned polypeptide. The present invention also relates to a pharmaceutical composition comprising the aforementioned polypeptide, and a raw material or a processed product in which the aforementioned polypeptide is removed or reduced. Furthermore, the present invention relates to a method for producing the processed product in which the aforementioned polypeptide is removed or reduced. Furthermore, the present invention also relates to a tester for determining the presence or absence of an antigen comprising the aforementioned polypeptide in an object.

BACKGROUND ART

IgE antibodies specific to a particular antigen (hereinafter also referred to as an allergen) are produced in the blood and tissue of an allergic patient. Physiological consequence resulting from the interaction between these IgE antibodies and the particular antigens causes an allergic reaction. Antigen means, in a broad sense, a food product or a food material that causes an allergic symptom, and means, in a narrow sense, a protein that is contained in, a food product or a food material and is bound by a specific IgE antibody (hereinafter the protein is also referred to as an allergen component).

In the case of a conventional allergy test agent, an antigen reagent is often prepared by simply grinding a food product, a food material, and the like that are potential allergens (Patent Literature 1). Therefore, only when, among various proteins that are contained in the conventional antigen reagent, a protein with a content above a threshold value, at which a positive reaction for IgE antibody binding can be determined, is an allergen component, the positive reaction in the allergy test can be detected. Thus, the diagnostic efficiency was not sufficiently high.

Several allergen components were found in the food product, the food material, and the like that are potential allergens and have been commercialized and comprised in a test kit. However, comprehensive identification of the allergen components is necessary to raise the reliability of the allergy test and the detection rate of patients by measurement of the above-mentioned allergen components is still not high enough.

In contrast, using a polypeptide comprising an epitope allows for diagnosis that takes even cross-reactivity (or also referred to as cross-antigenicity) into account, since the allergen-specific IgE antibody recognizes and binds to the epitope, which is a specific amino acid sequence in the allergen component. However, although there are a few cases in which the epitope of the allergen component was analyzed (Non Patent Literature 1), currently there are only very small number of cases. Furthermore, no kit for diagnosing allergy that uses an epitope is commercially available at present.

CITATION LIST

Patent Literature

PTL 1: JP 2002-286716 A

Non Patent Literature

NPL 1: Matsuo, H., et al., J. Biol. Chem., (2004), Vol. 279, No. 13, pp. 12135-12140

SUMMARY OF INVENTION

Technical Problem

The present invention provides a polypeptide comprising an epitope of an antigen. The present invention also provides a kit and a composition, and a method for diagnosing allergy, wherein the kit and the composition comprise the aforementioned polypeptide and the method uses the aforementioned polypeptide. The present invention also provides a pharmaceutical composition comprising the aforementioned polypeptide, and a raw material or a processed product in which the antigen comprising the aforementioned polypeptide is removed or reduced. Furthermore, the present invention relates to a method for producing the processed product in which the aforementioned antigen is removed or reduced. Furthermore, the present invention also provides a tester for determining the presence or absence of an antigen comprising the aforementioned polypeptide in an object.

Solution to Problem

In order to solve the above-mentioned problems, the present inventors conducted dedicated research on an epitope of ω-5 gliadin, which is a major antigen in wheat-dependent exercise-induced anaphylaxis (WDEIA), one form of an allergic reaction to wheat. As a result, the present inventors successfully discovered the epitope.

An epitope has a relatively short amino acid sequence. Therefore, when an identical amino acid sequence is found in a different allergen component, the aforementioned IgE antibody can bind to a plurality of allergen components. When common epitopes exist in different allergen components, the IgE antibody from an allergic patient binds to both epitopes, and thus, the antigen has cross-reactivity. Accordingly, the epitope identified by the present application allows for diagnosis and treatment of allergy including cross-reactive allergy, and detection of the plurality of allergen components comprising the aforementioned epitope, and the like.

The present invention has been accomplished based on the aforementioned finding. In other words, in another aspect, the present invention may be as described below.

[1] A polypeptide that specifically binds to an IgE antibody from an allergic patient, wherein the polypeptide comprises at least one amino acid sequence selected from the group consisting of SEQ ID NOs: 1 to 14.

[2] The polypeptide according to [1], wherein the polypeptide has 500 or less amino acid residues.

[3] A kit for diagnosing allergy, the kit comprising at least one polypeptide according to [1] or [2].

[4] A composition for diagnosing allergy, the composition comprising, as an antigen, at least one polypeptide according to [1] or [2]. [5] A method for providing an indicator for diagnosing allergy in a subject, the method comprising the following steps:
(i) contacting a sample obtained from the subject with an antigen, wherein the sample is a solution containing an IgE antibody;
(ii) detecting binding between the IgE antibody in the sample obtained from the subject and the antigen; and
(iii) providing an indicator of the fact that the subject has allergy, when the binding between the IgE antibody from the subject and the antigen is detected;
wherein the antigen is at least one polypeptide according to [1] or [2].

[6] A pharmaceutical composition comprising at least one polypeptide according to [1] or [2].

[7] The pharmaceutical composition according to [6], wherein the pharmaceutical composition is used for treating allergy.

[8] A tester for determining the presence or absence of an antigen in an object, wherein the tester includes an antibody that binds to at least one polypeptide according to [1] or [2].

[9] A raw material or a processed product in which an antigen is removed or reduced in the raw material or the processed product, wherein the antigen is at least one polypeptide according to [1] or [2].

[10] A method for producing a processed product in which an antigen is removed or reduced, the method comprising the step of confirming whether the antigen is removed or reduced during a production process of the processed product, wherein the antigen is at least one polypeptide according to [1] or [2].

[11] A tester for determining the presence or absence of an antigen in an object that causes an allergy, wherein the tester comprises a primer comprising a part of a nucleotide sequence of a nucleic acid encoding at least one polypeptide according to [1] or [2], and/or a part of a complementary strand thereof.

[12] A method for treating allergy comprising administering at least one polypeptide according to [1] or [2] to a patient in need of treatment of allergy.

[13] A method for treating a patient having allergy, the method comprising the steps of:
(a) determining whether a subject is a patient having allergy by:
  (i) administering at least one polypeptide according to [1] or [2] to the subject;
  (ii) monitoring reaction of the subject; and
  (iii) determining that the subject is a patient having allergy, when the subject shows a reaction;
and
(b) if the subject is a patient having allergy, then administering at least one polypeptide according to [1] or [2] to the patient.

[14] A method for treating a patient having allergy, the method comprising the steps of:
(a) determining whether a subject is a patient having allergy by:
  (i) contacting a sample obtained from the subject with an antigen, wherein the sample is a solution containing an IgE antibody;
  (ii) detecting binding between the IgE antibody in the sample obtained from the subject and the antigen; and
  (iii) determining that the subject is a patient having allergy, when the binding between the IgE antibody from the subject and the antigen is detected;
and
(b) if the subject is a patient having allergy, then administering at least one polypeptide according to [1] or [2] to the patient. [15] Use of the polypeptide according to [1] or [2] for producing a diagnostic agent or treating agent of allergy.

[16] A method for determining the presence or absence of an antibody that binds to an antigen in a subject, comprising the following steps:
(i) contacting at least one polypeptide according to [1] or [2] with a sample obtained from the subject;
(ii) detecting binding between at least one polypeptide according to [1] or [2] and an antibody in the sample obtained from the subject; and
(iii) determining the presence of the antibody that binds to the antigen in the subject, when the binding between at least one polypeptide according to [1] or [2] and the antibody was detected.

Advantageous Effects of Invention

The present invention can provide a novel polypeptide comprising an epitope of an antigen. Use of the polypeptide of the present invention allows for providing a highly sensitive kit, a composition, and a method for diagnosing allergy, a pharmaceutical composition comprising the aforementioned polypeptide, a tester for determining the presence or absence of an antigen comprising the aforementioned polypeptide in an object, and a raw material or a processed product in which the aforementioned polypeptide is removed or reduced and a method for producing the processed product.

BRIEF DESCRIPTION OF DRAWINGS

FIG. 1 is a diagram showing the result of chemiluminescent measurement using human serum of spots of peptides having an amino acid sequence of SEQ ID NO: 6 and SEQ ID NO: 13 in a prepared peptide array. P1 to P3 denote that the sera from WDEIA patients 1 to 3 were used, and N1 and N2 denote that the sera from healthy individuals 1 and 2 were used.

DESCRIPTION OF EMBODIMENTS

Figure 2:
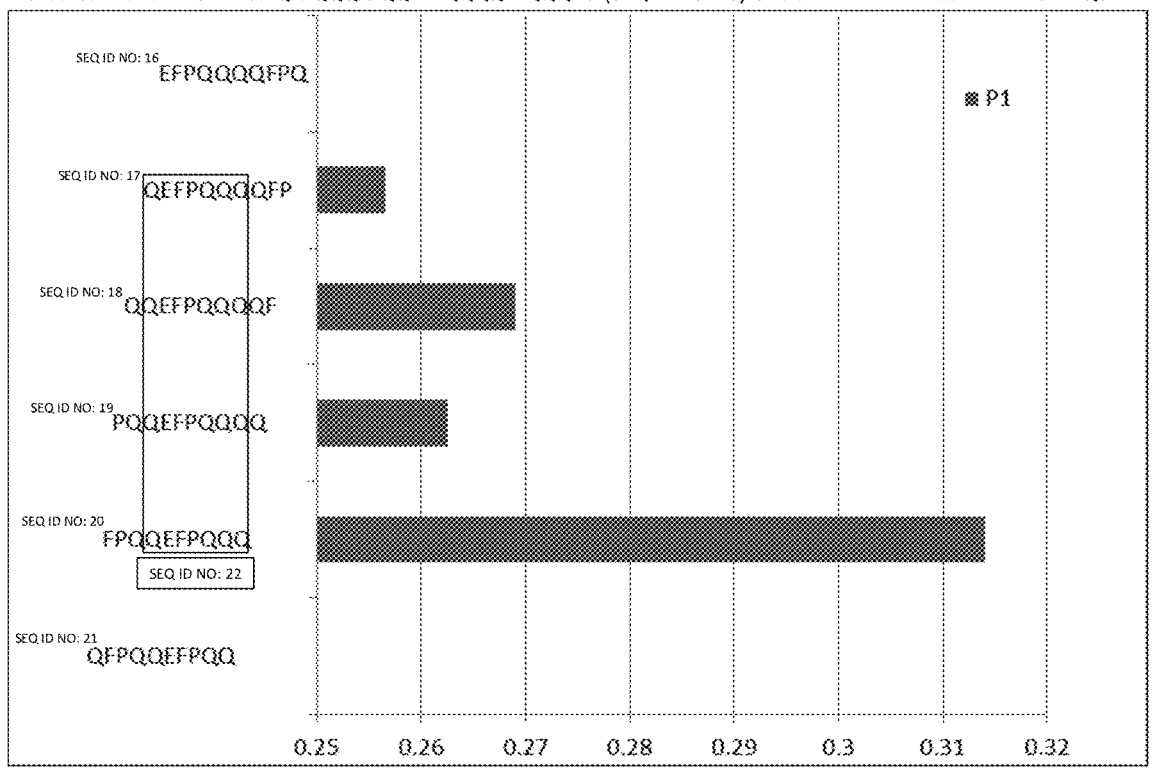
FIG. 2 is a diagram showing the result of identification of peptides (SEQ ID NOs: 22 and 29) having a minimal number of amino acids that serve as an epitope in SEQ ID NOs: 15 and 23 in a full-length amino acid sequence of ω-5 gliadin from bread wheat (UniProt accession number: Q40215, SEQ ID NO: 51) by an overlapping technique. The number on the horizontal axis denotes a value of coloration intensity at 450 nm measured by an absorption spectrometer (Abs.). P1 denotes that the serum from patient 1 was used.
Figure 2:
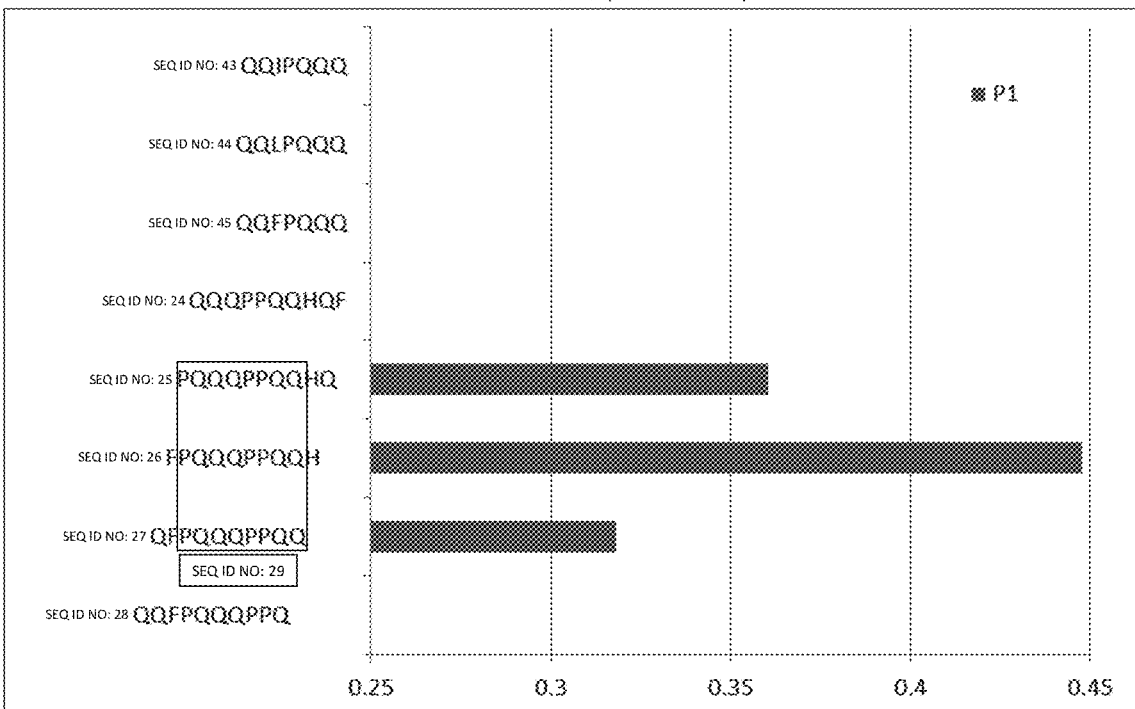

The present invention will now be described specifically below, but the present invention is not limited thereto.

Unless otherwise defined herein, scientific terms and technical terms used in connection with the present invention shall have the meanings that are commonly understood by those of skill in the art.

As used herein, allergy refers to a state of showing a hypersensitive reaction disadvantageous to an organism, wherein the hypersensitive reaction occurs to the organism previously sensitized to an antigen when the antigen re-enters into the organism. Contact with the antigen or ingestion of the antigen may cause an allergic reaction. In this context, contact means touching a substance, and particularly when used for a human body, means that the substance adheres to skin, a mucosa (such as an eye or a lip), and the like. Ingestion means taking something into a body by means such as inhalation or oral ingestion. Generally, an allergic reaction that occurs when food was ingested is particularly referred to as a food allergy. In a preferred embodiment, an allergy may be a food allergy. An IgE antibody is involved in many food allergies and the IgE antibody binds to a mast cell, a basophil, and the like. Once an antigen re-enters into an allergic patient's body, the antigen combines with the IgE antibody bound to the mast cell, the basophil, and the like, thereby leading to a physiological effect of an interaction between the IgE antibody and the antigen. Examples of these physiological effects include release of histamine, serotonin, heparin, an eosinophil chemotactic factor, various leukotrienes, or the like. These released substances cause the allergic reaction resulting from a combination of the IgE antibody and the particular antigen. Specifically, the IgE antibody recognizes and binds to an epitope, a particular amino acid sequence in the particular antigen, and the allergic reaction caused by the antigen develops through the above-mentioned process.

The allergy to which the present invention is directed to is not limited to a particular allergy and may be any allergy to the antigen comprising the epitope to be used. Examples of such allergy may include an allergy to a plant belonging to Poaceae, Brassicaceae, Rosaceae, Caricaceae, Leguminosae, Vitaceae, Juglandaceae, Euphorbiaceae, Amaranthaceae, Bromeliaceae, Solanaceae, Asparagaceae, Cucurbitaceae, Rutaceae, Cupressaceae, or Betulaceae, or a fungus belonging to Trichocomaceae. Examples of the plant of Poaceae include bread wheat (*Triticum aestivum* (scientific name)), einkorn wheat (*Triticum monococcum* (scientific name)), *Triticum dicoccoides* (scientific name), and *urartu* wheat (*Triticum urartu* (scientific name)) of the genus *Triticum*; Tausch's goatgrass (*Aegilops tauschii* (scientific name)) and *Aegilops uniaristata* (scientific name) of the genus *Aegilops*; *Thinopyrum elongatum* (scientific name) of the genus *Thinopyrum*; *Psathyrostachys juncea* (scientific name) of the genus *Psathyrostachys*; a sorghum (*Sorghum bicolor* (scientific name)) of the genus *Sorghum*, and the like. Examples of the plant of Brassicaceae include a colza (*Brassica napus* (scientific name)) of the genus *Brassica* and a radish (*Raphanus sativus* (scientific name)) of the genus *Raphanus*. Examples of the plant of Rosaceae include a sweet cherry (*Prunus avium* (scientific name)) and a Japanese apricot (*Prunus mume* (scientific name)) of the genus *Prunus*, and a peach (*Prunus persica* (scientific name)) of the genus *Amygdalus*; an apple (*Malus domestica* (scientific name)) of the genus *Malus*, and the like. Examples of the plant of Caricaceae include a papaya (*Carica papaya* (scientific name)) of the genus *Carica*, and the like. Examples of the plant of Leguminosae include a pigeon pea (*Cajanus cajan* (scientific name)) of the genus *Cajanus*; an azuki bean (*Vigna angularis* (scientific name)) of the genus *Vigna*; a soybean (*Glycine max* (scientific name)) and a wild soybean (*Glycine soja* (scientific name)) of the genus *Glycine*; a kidney bean (*Phaseolus vulgaris* (scientific name)) of the genus *Phaseolus*; a chick pea (*Cicer arietinum* (scientific name)) of the genus *Cicer*; and the like. Examples of the plant of Vitaceae include a European grape (*Vitis vinifera* (scientific name)) of the genus *Vitis*. Examples of the plant of Juglandaceae include a Shinano walnut (*Juglans regia* (scientific name)) of the genus *Juglans*. Examples of the plant of Euphorbiaceae include a cassava (*Manihot esculenta* (scientific name)) of the genus *Manihot*; a hevea (*Hevea brasiliensis* (scientific name)) of the genus *Hevea*, and the like. Examples of the plant of Amaranthaceae include a quinoa (*Chenopodium quinoa* (scientific name)) of the genus *Chenopodium*; spinach (*Spinacia oleracea* (scientific name)) of the genus *Spinacia*, and the like. Examples of the plant of Bromeliaceae include a pineapple (*Ananas comosus* (scientific name)) of the genus *Ananas*, and the like. Examples of the plant of Solanaceae include a potato (*Solanum tuberosum* (scientific name)) of the genus *Solanum* and the like. Examples of the plant of Asparagaceae include an asparagus (*Asparagus officinalis* (scientific name)) of the genus *Asparagus*, and the like. Examples of the plant of Cucurbitaceae include a melon (*Cucumis melo* (scientific name)) of the genus *Cucumis*, and the like. Examples of the plant of Rutaceae include an orange (*Citrus sinensis* (scientific name)); a clementine (*Citrus clementina* (scientific name)) of the genus *Citrus*, and the like. Examples of the plant of Cupressaceae include a Japanese cedar (*Cryptomeria japonica* (scientific name)) of the genus *Cryptomeria*, and the like. Examples of the plant of Betulaceae include a Japanese white birch (*Betula platyphylla* (scientific name)) of the genus *Betula*, and the like. Examples of the fungus of Trichocomaceae include *Aspergillus turcosus* (scientific name) of the genus *Aspergillus*, and the like.

As used herein, allergy to wheat refers to a state of having an allergic reaction to a protein and the like, which acts as an antigen, contained in a plant belonging to the tribe Triticeae (scientific name) The tribe Triticeae includes the genus *Triticum* (scientific name) such as bread wheat, club wheat (*Triticum compactum* (scientific name)), and durum wheat (*Triticum durum* (scientific name)); the genus *Aegilops* (scientific name) such as Tausch's goatgrass; and the genus *Thinopyrum* (scientific name) such as *Thinopyrum elongatum*. In a preferred embodiment, the allergic reaction to wheat may be wheat-dependent exercise-induced anaphylaxis. ω-5 gliadin is known to be involved in this anaphylaxis as a main antigen.

Hereinbelow, antigen as used herein refers to a substance that causes an allergic reaction and is also referred to as an allergen component. Preferably, the antigen is a protein.

As used herein, protein is a molecule having a structure in which amino acids are linked by a peptide bond. The number of amino acids comprised in the protein is not limited to a particular number. As used herein, the term "polypeptide" also means a molecule having a structure in which amino acids are linked by a peptide bond. The number of amino acids comprised in the polypeptide is not limited to a particular number. "Polypeptide" is an expression encompassing "protein". In some cases, a polypeptide consisting of about 2 to 50 amino acids linked by peptide bonds is particularly referred to as a peptide. Furthermore, when an amino acid may have optical isomers, the amino acid is in L-form, unless otherwise specifically indicated. The notation of amino acid sequences of proteins, polypeptides, or peptides used in this specification is based on the notation that is a standard method and commonly used in the industry. Thus, the amino acid sequence is represented by a one-letter code of amino acids, with the amino terminus on the left and the carboxy terminus on the right. In this context, X used in the one-letter code of amino acids may be any substance provided that the substance has an amino group and a carboxyl group capable of binding to amino acids on both sides. In particular, X represents that it may be any of 20 natural amino acids.

As used herein, "substituted by another amino acid" means that an amino acid is substituted by an amino acid different from the amino acid in the original sequence. In a preferred embodiment, substitution is conservative substitution. Conservative substitution is a substitution of a certain amino acid residue by a residue having a similar physicochemical characteristic. Conservative substitution may be any substitution as long as it does not substantially change the structural characteristic of the original sequence. For example, conservative substitution may be any substitution as long as the substituting amino acid neither destroys a helix present in the original sequence nor destroys a different type of secondary structure characterizing the original sequence. Hereinbelow, conservative substitution of amino acid residues is illustrated by grouping intersubstitutable residues; however, the intersubstitutable amino acid residues are not limited to those described below.

Group A: leucine, isoleucine, valine, alanine, methionine
Group B: aspartic acid, glutamic acid
Group C: asparagine, glutamine
Group D: lysine, arginine
Group E: serine, threonine
Group F: phenylalanine, tyrosine For nonconservative substitution, a member of one of the above-mentioned groups can be substituted by a member of a different group. For example, an amino acid of the abovementioned Groups B, D, and E may be substituted by an amino acid of other groups for precluding accidental glycosylation. As another example, cysteine may be deleted or substituted by a different amino acid for preventing cysteine from being folded in the tertiary structure of protein. As still another example, for maintaining the balance between hydrophilicity and hydrophobicity or increasing hydrophilicity to facilitate synthesis, an amino acid may be substituted by taking a hydropathy scale of an amino acid, that is, an index of hydrophobicity and hydrophilicity of an amino acid (J. Kyte and R. Doolittle, J. Mol. Biol., Vol. 157, p. 105-132, 1982) into account.

In another embodiment, substitution of an amino acid by another amino acid with less steric hindrance compared to the original amino acid, such as substitution of Group F by Groups A, B, C, D, or E; and substitution of a charged amino acid by an uncharged amino acid, such as substitution of Group B by Group C may be performed. Such substitutions may enhance binding activity to the IgE antibody.

In this specification, a percent identity between two amino acid sequences can be determined by visual test and mathematical calculation. The percent identity can also be determined by using a computer program. Examples of such computer programs include BLAST, FASTA (Altschul et al., J. Mol. Biol., 215: 403-410 (1990)), ClustalW, and the like. In particular, various conditions (parameters) for identity search by the BLAST program are those described by Altschul et al. (Nucl. Acids. Res., 25, p. 3389-3402, 1997) and are publicly available from the website of, for example, the National Center for Biotechnology Information (NCBI) and the DNA Data Bank of Japan (DDBJ) (BLAST manual, Altschul et al. NCB/NLM/NIH Bethesda, Md. 20894; Altschul et al.). Furthermore, the percent identity can be determined by using a program such as a genetic information processing software GENETYX Ver. 7 (GENETYX CORPORATION), DNASIS Pro (Hitachi Software), and Vector NTI (Infomax).

Epitope of Antigen

As shown in Examples 1 and 2, an epitope in ω-5 gliadin and an amino acid within the epitope important for binding activity to an IgE antibody from an allergic patient were identified.

The present invention provides a polypeptide comprising an amino acid sequence that specifically binds to an IgE antibody from an allergic patient, the polypeptide being selected from the group consisting of the following (1) to (6):

(1) a polypeptide comprising at least one amino acid sequence selected from the group consisting of SEQ ID NOs: 6 and 13;

(2) a polypeptide comprising an amino acid sequence of XEXPXXQ (SEQ ID NO: 1), preferably QEXPXXQ (SEQ ID NO: 2), more preferably QEXPXQQ (SEQ ID NO: 3), even more preferably QXEXPXXQ (SEQ ID NO: 4), and most preferably FPQXEXPXXQ (SEQ ID NO: 5);

(3) a polypeptide comprising an amino acid sequence of PXQXXPQQ (SEQ ID NO: 8), preferably PQQXXPQQ (SEQ ID NO: 9), more preferably FPXQXXPQQ (SEQ ID NO: 10), even more preferably PXQXXPQQH (SEQ ID NO: 11), and most preferably FPXQXXPQQH (SEQ ID NO: 12);

(4) a polypeptide comprising an amino acid sequence in which any one, two, three, or four amino acids of the amino acids corresponding to amino acids at positions 1, 3, 5, and 6 in QEFPQQQ (SEQ ID NO: 22) are substituted by another amino acid, preferably alanine, preferably, a polypeptide comprising an amino acid sequence in which any one, two, or three amino acids of the amino acids corresponding to amino acids at positions 3, 5, and 6 in SEQ ID NO: 22 are substituted by another amino acid, preferably alanine, more preferably, a polypeptide comprising an amino acid sequence in which any one or two amino acids of the amino acids corresponding to amino acids at positions 3 and 5 in SEQ ID NO: 22 are substituted by another amino acid, preferably alanine, even more preferably, a polypeptide comprising an amino acid sequence in which any one, two, three, or four amino acids of the amino acids corresponding to amino acids at positions 2, 4, 6, and 7 in QQEFPQQQ (SEQ ID NO: 46) are substituted by another amino acid, preferably alanine, most preferably, a polypeptide comprising an amino acid sequence in which any one, two, three, or four amino acids of the amino acids corresponding to amino acids at positions 4, 6, 8, and 9 in FPQQEFPQQQ (SEQ ID NO: 47) are substituted by another amino acid, preferably alanine; (5) a polypeptide comprising an amino acid sequence in which any one, two, or three amino acids of the amino acids corresponding to amino acids at positions 2, 4, and 5 in PQQQPPQQ (SEQ ID NO: 29) are substituted by another amino acid, preferably alanine, preferably, a polypeptide comprising an amino acid sequence in which any one or two amino acids of the amino acids corresponding to amino acids at positions 4 and 5 in SEQ ID NO: 29 are substituted by another amino acid, preferably alanine, more preferably, a polypeptide comprising an amino acid sequence in which any one, two, or three amino acids of the amino acids corresponding to amino acids at positions 3, 5, and 6 in FPQQQPPQQ (SEQ ID NO: 48) are substituted by another amino acid, preferably alanine, even more preferably, a polypeptide comprising an amino acid sequence in which any one, two, or three amino acids of the amino acids corresponding to amino acids at positions 2, 4, and 5 in PQQQPPQQH (SEQ ID NO: 49) are substituted by another amino acid, preferably alanine, most preferably, a polypeptide comprising an amino acid sequence in which any one, two, or three amino acids of the amino acids corresponding to amino acids at positions 3, 5, and 6 in FPQQQPPQQH (SEQ ID NO: 50) are substituted by another amino acid, preferably alanine; and (6) a polypeptide comprising at least one amino acid sequence selected from the group consisting of SEQ ID NOs: 7 and 14.

It is noted that the polypeptide of said sequences (1) to (6) may not include a variant that is identical to or has 90% or more, 80% or more, or 70% or more identity to a full-length amino acid sequence of ω-5 gliadin from bread wheat (SEQ ID NO: 51).

SEQ ID NOs: 6 and 13 correspond to amino acids 221 to 235 (SEQ ID NO: 6) and 161 to 175 (SEQ ID NO: 13) of the full-length amino acid sequence of ω-5 gliadin from bread wheat (SEQ ID NO: 51), respectively.

The residue represented by X in the above-mentioned polypeptides (2) and (3) is an amino acid residue at a position where binding activity to the IgE antibody from the allergic patient was retained when the residue was substituted by alanine by an alanine scanning technique (Non Patent Literature 1) described in Example 1. It is well known to those of skill in the art that such position has a high probability of retaining the binding activity to the IgE antibody when the residue thereat was substituted by any other amino acid.

The length of the above-mentioned polypeptides of (1) to (6) is not limited to a particular length. In a preferred embodiment, the above-mentioned polypeptides of (1) to (6) may be 1000 amino acids or less, 700 amino acids or less, 500 amino acids or less, 300 amino acids or less, 200 amino acids or less, 100 amino acids or less, 50 amino acids or less, 30 amino acids or less, 20 amino acids or less, 10 amino acids or less, or 5 amino acids or less in length.

The above-mentioned polypeptides of (1) to (6) may be prepared by a chemical synthesis technique such as solid-phase synthesis of peptides. Alternatively, a polypeptide comprising an epitope may be obtained by expressing the polypeptide as a recombinant protein by a genetic recombination technique well known to those of skill in the art and then separating and purifying the expressed protein by a protein purification method well known to those of skill in the art.

Diagnostic Kit and Diagnostic Method

The present invention provides a method for providing an indicator for diagnosing allergy in a subject, the method comprising the following steps:

(i) contacting a sample obtained from the subject with an antigen, wherein the sample is a solution containing an IgE antibody;
(ii) detecting binding between the IgE antibody in the sample obtained from the subject and the antigen; and
(iii) providing an indicator of the fact that the subject has allergy, when the binding between the IgE antibody from the subject and the antigen is detected;
wherein the antigen is a polypeptide that is at least one of the above-mentioned polypeptides according to (1) to (6) or a polypeptide composed of two or more of the above-mentioned polypeptides according to (1) to (6) that are linked together with or without a spacer.

Hereinbelow, the polypeptide that is at least one of the above-mentioned polypeptides according to (1) to (6) or the polypeptide composed of two or more of the above-mentioned polypeptides according to (1) to (6) linked together with or without a spacer is described herein as "an antigen comprising the above-mentioned (1) to (6)". The type of spacer is not particularly limited, and spacers commonly used by those of skill in the art for linking a plurality of peptides can be used. The spacer may be, for example, a hydrocarbon chain such as Acp(6)-OH.

The sample obtained from the subject is a solution containing an Ig antibody, particularly an IgE antibody, collected from the subject. Examples of such solution include blood, saliva, sputum, nasal discharge, urine, sweat, a tear, and the like. The sample obtained from the subject may be subjected to pretreatment for increasing the IgE antibody concentration in the sample before contacting the sample with an antigen comprising the above-mentioned (1) to (6). Examples of the sample pretreatment may include obtaining a blood serum or blood plasma from blood. Furthermore, a Fab portion may be purified, which is a portion the binds to the antigen comprising the above-mentioned (1) to (6). In a particularly preferred embodiment, the above-mentioned step (i) is performed by contacting the IgE antibody in the serum obtained from the subject with the antigen.

The IgE antibody may be an IgE antibody itself or may be a mast cell with an IgE antibody bound thereto, and the like.

Contacting the sample obtained from the subject with the antigen comprising the above-mentioned (1) to (6) and detecting the binding therebetween can be performed by an already known method. Examples of such method may include detection by ELISA (Enzyme-Linked Immunosorbent Assay), a sandwich immunoassay, immunoblotting, immunoprecipitation, and immunochromatography can be used. All of these are techniques in which binding between the antigen comprising the above-mentioned (1) to (6) and the IgE antibody from the subject is detected by contacting the IgE antibody from the subject with the antigen comprising the above-mentioned (1) to (6) to allow the antibody to bind the antigen; allowing an enzyme-labeled secondary antibody to act on the IgE antibody specifically binding to the antigen comprising the above-mentioned (1) to (6); and adding an enzyme substrate (generally, a chromogenic or luminescent reagent) and detecting a product of the enzymatic reaction. Alternatively, such method is a method by detecting a fluorescently labeled secondary antibody. Alternatively, detection by a measuring method such as surface plasmon resonance (SPR) that can assess binding between the antigen comprising the above-mentioned (1) to (6) and the IgE antibody can also be used. Plural kinds of IgE antibodies specific to the antigen comprising the above-mentioned (1) to (6) may be mixed.

The antigen comprising the above-mentioned (1) to (6) may be immobilized on a carrier. In this case, ELISA, sandwich immunoassay, immunochromatography, surface plasmon resonance and the like can be used in the above-mentioned steps (i) and (ii). The above-mentioned step (i) is performed by contacting the sample obtained from the subject with a surface on which the antigen comprising the above-mentioned (1) to (6) was immobilized. Alternatively, the IgE antibody from the subject immobilized on the carrier may be used and binding between the IgE antibody and the antigen comprising the above-mentioned (1) to (6) may be detected by the above-mentioned technique.

The antigen comprising the above-mentioned (1) to (6) may not be immobilized on the carrier. In this case, flow cytometry and the like can be used in the above-mentioned steps (i) and (ii) and presence of the antigen comprising the above-mentioned (1) to (6) bound by the IgE antibody can be confirmed by a laser beam. Examples of this method may include a basophil activation test (BAT), which is a method of detecting a surface antigen CD203c that appears when a basophil was activated by contact with the antigen comprising the above-mentioned (1) to (6). Furthermore, examples may include a histamine release test (HRT), which examines whether histamine is released or not when the antigen comprising the above-mentioned (1) to (6) is further contacted with a hemocyte in the sample as well.

The antigen comprising the above-mentioned (1) to (6) is an antigen that specifically binds to the IgE antibody from the allergic patient. Therefore, when binding between the IgE antibody from the subject and the aforementioned antigen was detected, an indicator of the subject having allergy is provided.

The present invention also provides a kit for diagnosing allergy, the kit comprising at least one of the antigens comprising the above-mentioned (1) to (6). The kit of the present invention may be used for the above-mentioned method for providing the indicator for diagnosing allergy or the method for diagnosing allergy described below. The kit of the present invention comprises at least one of the antigens comprising the above-mentioned (1) to (6) and may further comprise an enzyme-labeled anti-IgE antibody and a chromogenic substrate or a luminescent substrate serving as a substrate for the enzyme. Alternatively, a fluorescently labeled anti-IgE antibody may be used. In the kit of the present invention, the antigen comprising the above-mentioned (1) to (6) may be provided in a state immobilized on a carrier. The kit of the present invention may also be provided together with instructions about procedures for diagnosis and a package comprising the instructions.

In another embodiment, the above-mentioned kit includes a companion diagnostic agent for allergy. A companion diagnostic agent is used for identifying a patient for whom a medicament is expected to be effective or identifying a patient who is at risk of a serious side effect caused by the medicament, or assessing reactivity of the medicament for optimizing treatment using the medicament. In this context, optimization of treatment includes, for example, determination of a dosage regimen and determination of discontinuation of administration, and confirmation of an allergen component to be used for establishing immune tolerance.

The present invention also provides a composition for diagnosing allergy, the composition comprising at least one of the antigens comprising the above-mentioned (1) to (6). The composition of the present invention can be used for a method for diagnosing allergy described below. The composition of the present invention may comprise a commonly used pharmaceutically acceptable carrier or additive with the antigen of the present invention, if required.

In one aspect, the present invention provides a method for diagnosing allergy in a subject "in vitro," the method comprising the following steps:
(i) contacting a sample obtained from the subject with an antigen;
(ii) detecting binding between the IgE antibody in the sample obtained from the subject and the antigen; and
(iii) determining that the subject has allergy, when the binding between the IgE antibody from the subject and the antigen is detected;
wherein the antigen is at least one of the proteins identified as the antigen comprising the above-mentioned (1) to (6). In this method, the steps (i) and (ii) are performed as described about the steps of the method for providing an indicator for diagnosing allergy.

In another aspect, the present invention provides a method for diagnosing allergy in a subject "in vivo," the method comprising administering at least one of the antigens comprising the above-mentioned (1) to (6) to the subject. The aforementioned method may be performed in a skin test form comprising applying the antigen comprising the above-mentioned (1) to (6) to skin. Examples of the skin test types include a prick test by applying a composition for diagnosing allergy on skin, followed by making a small prick to the extent that no bleeding occurs, thereby allowing the antigen comprising the above-mentioned (1) to (6) to permeate the skin, and monitoring skin reaction; a scratch test by applying the composition, followed by scratching skin lightly, and monitoring reaction; a patch test by applying the composition in a form such as a cream or an ointment on skin and monitoring reaction; and an intradermal test by administering the antigen comprising the above-mentioned (1) to (6) intradermally and monitoring reaction, and the like. When skin reaction such as swelling of the skin area where the antigen comprising the above-mentioned (1) to (6) was applied occurred, the subject will be diagnosed as having an allergy. In this context, the amount of the antigen comprising the above-mentioned (1) to (6) to be applied on skin may be, for example, 100 μg or less per dose.

For diagnosis of allergy, a challenge test for identifying an antigen is often performed. At least one of the antigens comprising the above-mentioned (1) to (6) can be used as an active ingredient in the challenge test for diagnosing allergy. In this context, the allergen component to be used in the challenge test may be an expressed and purified polypeptide. For example, the allergen component may be a polypeptide expressed in a food product or a food material, such as pollen rice produced by transferring a gene of a cedar pollen antigen into a rice plant and expressing the antigen protein in a rice grain.

In another aspect, the present invention provides at least one of the antigens comprising the above-mentioned (1) to (6) for using in diagnosis of allergy.

In still another aspect, the present invention provides use of at least one of the antigens comprising the above-mentioned (1) to (6) for producing a diagnostic agent of allergy.

In this section, the allergy to be diagnosed or detected may be an allergy to the antigen comprising the above-mentioned (1) to (6). Thus, detection of an allergy may be not only detection of an allergy to a single antigen selected from the antigens comprising the above-mentioned (1) to (6) but also detection of an allergy comprising a cross-reactive allergy.

Pharmaceutical Composition and Treatment Method

The present invention provides a pharmaceutical composition comprising at least one of the antigens comprising the above-mentioned (1) to (6). In one embodiment, the above-mentioned pharmaceutical composition is used for treating allergy. Treating allergy is increasing the limit dose of an antigen which does not lead to allergy onset when the antigen was taken into a body, and is ultimately aimed at achieving a state where an ordinal amount of intake of the antigen does not lead to allergy onset (remission).

The present invention also provides a method for treating allergy comprising administering at least one of the antigens comprising the above-mentioned (1) to (6) to a patient in need of treatment of allergy.

In another aspect, the present invention provides a method for treating a patient having allergy, the method comprising the steps of: (a) determining whether a subject is a patient with an allergy by: (i) administering at least of the antigens comprising the above-mentioned (1) to (6) to the subject; (ii) monitoring reaction of the subject; and (iii) determining that the subject is a patient having allergy, when the subject shows a reaction; and (b) if the subject is a patient having allergy, then administering at least of the antigens comprising the above-mentioned (1) to (6) to the patient.

In yet another aspect, the present invention provides a method for treating a patient having allergy, the method comprising the steps of: (a) determining whether a subject is a patient having allergy by: (i) contacting a sample obtained from the subject with an antigen, wherein the sample is a solution containing an IgE antibody; (ii) detecting binding between the IgE antibody in the sample obtained from the subject and the antigen; and (iii) determining that the subject is a patient having allergy, when the binding between the IgE antibody from the subject and the antigen was detected; and (b) if the subject is a patient having allergy, then administering at least of the antigens comprising the above-mentioned (1) to (6) to the patient.

In further aspect, the present invention provides at least one of the antigens comprising the above-mentioned (1) to (6) for use in treatment of allergy. In still another aspect, the present invention provides use of at least one of the antigens comprising the above-mentioned (1) to (6) for producing a treating agent of allergy.

In treatment of allergy, hyposensitization therapy is often performed, which is aimed at inducing immune tolerance by administering an antigen to a patient. At least one of the antigens comprising the above-mentioned (1) to (6) can be used as an active ingredient in the hyposensitization therapy for allergy. In this context, an allergen component to be used in the hyposensitization therapy may be an expressed and purified polypeptide. For example, the allergen component may be a polypeptide expressed in a food product or a food material, such as pollen rice.

The pharmaceutical composition of the present invention can be administered by an ordinal administration route. Examples of the ordinal administration route include oral administration, sublingual administration, transdermal administration, intradermal administration, subcutaneous administration, administration into blood, intranasal administration, intramuscular administration, intraperitoneal administration, and intrarectal administration.

The pharmaceutical composition of the present invention can be used as a pharmaceutical composition to which, in addition to the antigen comprising the above-mentioned (1) to (6), a commonly used pharmaceutically acceptable adjuvant, excipient, or various additives (for example, a stabilizer, a solubilizer, an emulsifying agent, a buffering agent, a preservative, a coloring agent, and the like) was added by a routine method as needed. The dosage form of the pharmaceutical composition may be selected as appropriate by those of skill in the art depending on the administration route. For example, the pharmaceutical composition may be in the form such as a tablet, a capsule, a troche, a sublingual tablet, an injection, an intranasal aerosol, a cataplasm, a solution, a cream, a lotion, and the like. The dosage, frequency of administration, and/or administration period of the pharmaceutical composition of the present invention can be selected as appropriate by a physician depending on the administration route, the symptom, the characteristics of the patient such as age and weight, and the like. For example, for an adult, the pharmaceutical composition may be administered at 100 μg or less per dose. The dosing interval may be roughly, for example, daily, weekly, twice a month, or once every three months. The administration period may be, for example, from several weeks to several years. The administration method may be a method by which the dosage is increased gradually during the administration period.

In this section, the allergy to be treated may be an allergy to the antigen comprising the above-mentioned (1) to (6). Thus, treatment of the allergy may be not only treatment of an allergy to a single antigen selected from the antigens comprising the above-mentioned (1) to (6) but also treatment of an allergy comprising a cross-reactive allergy.

Tester

The present invention provides a tester comprising an antibody against at least one of the antigens, the tester comprising the above-mentioned (1) to (6).

The antibody can be made by a routine method. For example, the antibody may be prepared by immunizing a mammal such as a rabbit with the antigen comprising the above-mentioned (1) to (6). The antibody may be an Ig antibody, a polyclonal antibody, a monoclonal antibody, or an antigen-binding fragment thereof (for example, Fab, F(ab')$_2$, and Fab').

In the above-mentioned tester, the antibody may be provided in a form bound to a carrier. The carrier is not limited to a particular carrier as long as it can be used for detecting binding between the antibody and the antigen comprising the above-mentioned (1) to (6). Any carrier known to those of skill in the art may be used. Furthermore, the antibody against the antigen comprising the above-mentioned (1) to (6) is preferably an antibody against the epitope described in the above section "Epitope of Antigen". This enables the tester to detect binding including cross-reactive binding.

Examples of a method for examining the presence or absence of the antigen comprising the above-mentioned (1) to (6) include the following methods:

a method comprising contacting a tester comprising the prepared antibody with a sample obtained from, for example, a raw material, a processed product, or the like, and detecting binding between the antibody and the antigen comprising the above-mentioned (1) to (6) in the sample by a method, for example, an ELISA method, and determining that the antigen remains in the raw material or the processed product of interest when the binding between the antibody and the antigen comprising the above-mentioned (1) to (6) was detected; and a method by impregnating a filter paper or the like with, for example, a raw material, a processed product, or the like, and allowing an antibody solution to react with the filter paper to detect the antigen comprising the above-mentioned (1) to (6) contained therein.

Another embodiment of the present invention includes a tester for determining the presence or absence of the antigen comprising the above-mentioned (1) to (6) in an object, the antigen causing allergy, wherein the tester comprises a primer corresponding to an epitope. Without limitation, for example, the above-mentioned primer may be designed to comprise a part of a nucleotide sequence of nucleic acid encoding any of the amino acid sequences specified in the above-mentioned (1) to (6) and/or a part of a complementary strand thereof. In a specific embodiment, when the antigen is ω-5 gliadin, the above-mentioned primer is designed to comprise a part of a nucleotide sequence of the full-length nucleotide sequence of a ω-5 gliadin gene (EMBL-Bank/ENA accession number: BAE20328.1, SEQ ID NO: 52) and/or a part of the complementary strand to the nucleotide sequence of SEQ ID NO: 52. For example, the primer is designed to have a nucleotide sequence of preferably 12 bases, 15 bases, 20 bases, or 25 bases derived from a sequence of the 5' end or the central part of the nucleotide sequence of SEQ ID NO: 52 and/or a sequence of the 5' end of the complementary strand to the nucleotide sequence of SEQ ID NO: 52; or a sequence of the 5' end of the nucleotide sequence set forth in SEQ ID NO: 52 and/or a sequence of the 5' end or the central part of the complementary strand to the nucleotide sequence of SEQ ID NO: 52. Furthermore, the above-mentioned primer may be designed to be a nucleotide sequence in a region upstream of a part encoding an epitope or a nucleotide sequence in a region upstream of a complementary strand to the part encoding the epitope, wherein the nucleotide sequences are in a nucleic acid encoding protein comprising the epitope which is any of the amino acid sequences specified in the above-mentioned (1) to (6). In this context, the position of the epitope in the full-length sequence when the antigen is ω-5 gliadin is as specified in the section "Epitope of Antigen" as described above. Furthermore, particularly when mRNA is a target, a primer complementary to a poly A tail may be comprised.

For example, the presence or absence of the antigen comprising the above-mentioned (1) to (6) is determined by amplifying DNA by PCR (Polymerase Chain Reaction) such as RT-PCR using said primer with DNA or mRNA obtained from a sample as a template; and determining whether or not an amplified DNA sequence comprises nucleic acid encoding any of the amino acid sequences specified in the above-mentioned (1) to (6). Examples of a method for amplifying mRNA, a target of amplification, by PCR may include a RACE technique. When one of the amino acid sequences encoded by three possible open reading frames in the amplified DNA comprises any of the amino acid sequences specified in the above-mentioned (1) to (6) (for example, SEQ ID NO: 1 or 8), it is determined to be antigenic. When such DNA is not amplified, it is determined to be not antigenic. In a specific embodiment, when the antigen is ω-5 gliadin, the presence or absence of the antigen is determined by comparing the amino acid sequences encoded by three possible open reading frames in the amplified DNA with SEQ ID NO: 22 or 29. When such DNA is not amplified, it is determined to be antigenic.

In one embodiment, the above-mentioned tester is used for examining the presence or absence of the antigen comprising the above-mentioned (1) to (6) in a raw material or an object on a manufacturing line of a processed product and the like. The raw material may be a food material, a raw material for a cosmetic product, a raw material for a medicament, or the like. The processed product may be a processed food, a cosmetic product, a medicament, or the like. The above-mentioned tester may be used for searching biological species contained as a raw material, testing quality of the manufacturing line and a product prior to shipment by a manufacturer, or self-checking the presence or absence of an antigen in a raw material or a processed product of interest by an eater or a user thereof.

It should be appreciated that the present invention also provides a method for determining the presence or absence of an antibody that binds to an antigen in a subject, comprising the following steps: (i) contacting at least one of the antigens comprising the above-mentioned (1) to (6) with a sample obtained from the subject; (ii) detecting binding between at least one of the antigens comprising the above-mentioned (1) to (6) and an antibody in the sample obtained from the subject; and (iii) determining the presence of the antibody that binds to the antigen in the subject, when the binding between at least one of the antigens comprising the above-mentioned (1) to (6) and the antibody is detected. The kit, composition, and tester for use in the method are also incorporated herein.

Raw Material with Allergen Removed and Others

The present invention provides a raw material or a processed product in which at least one of the antigens comprising the above-mentioned (1) to (6) is removed or reduced.

A method for removing or reducing the antigen of the present invention in the raw material or the processed product is not limited. Removal or reduction of the antigen may be performed by any method as long as the antigen comprising the above-mentioned (1) to (6) is removed or reduced.

Removal or reduction of at least one of the antigens comprising the above-mentioned (1) to (6) may be achieved by removing or reducing the entire antigen or may be achieved by cleaving or removing a sequence section specified by any of the above-mentioned (1) to (6) from an antigenic protein. "Removing" includes deletion and modification of all or part of the sequence section specified by any of the above-mentioned (1) to (6).

For example, the raw material in which the antigen comprising the above-mentioned (1) to (6) is removed or reduced may be prepared as a raw material in which expression of the antigen comprising the above-mentioned (1) to (6) was knocked out by using a gene knockout technique. Any technique known to those of skill in the art such as genetic modification can be used as the gene knockout technique.

The processed product in which the antigen comprising the above-mentioned (1) to (6) is removed or reduced may be a processed product produced by using a raw material in which the antigen comprising the above-mentioned (1) to (6) is removed or reduced, such as powdered milk produced by using purified peptide as the raw material. When an ordinal raw material is used, a process of removing or reducing the antigen comprising the above-mentioned (1) to (6) is performed before or after preparation of the processed product. Examples of a method for removing or reducing the antigen comprising the above-mentioned (1) to (6) in the processed product produced by using the ordinal raw material include a method of removing a protein component in the raw material by high pressure treatment, elution with a neutral salt solution, high-temperature steam, and the like, and a method of hydrolyzing or denaturing the antigen or altering an amino acid thereof (chemical modification or elimination of a side chain, or the like) by heat treatment and acid treatment. Examples of a method of cleaving the antigen comprising the above-mentioned (1) to (6) include a method of treating by cleaving the antigen with a specific digestive enzyme.

Production Method of Processed Product with Allergen Removed

The present invention provides a method for producing a processed product in which an antigen is removed or reduced, comprising the step of confirming whether the antigen is removed or reduced, or not, during a production process of the processed product, wherein the antigen is at least one of the antigens comprising the above-mentioned (1) to (6).

In the aforementioned production method, what an antigen is removed or reduced means that at least one of the antigens comprising the above-mentioned (1) to (6) is removed or reduced or that a sequence section specified by any of the above-mentioned (1) to (6) was cleaved or removed from said antigen.

A technique for confirming whether the antigen is removed or reduced, or not, during the production process of the processed product is not limited to a particular technique and any technique that can detect at least one of the antigens comprising the above-mentioned (1) to (6) may be used. For example, the presence or absence of the aforementioned polypeptide or antigen in the aforementioned processed product may be confirmed based on binding activity between a sample containing a material produced during the production process of the processed product and an antibody to at least one of the antigens comprising the above-mentioned (1) to (6). The detail of such method was described in the above section "Diagnostic Kit and Diagnostic Method". Specifically, in the above-mentioned production method, the technique described in the above section "Diagnostic Kit and Diagnostic Method" can be used for confirming whether the antigen is removed or reduced, or not, during the production process of the processed product; wherein "IgE antibody from the subject" in the above section "Diagnostic Kit and Diagnostic Method" is replaced with "antibody to at least one of the antigens comprising the above-mentioned (1) to (6)", and "antigen" in the above section "Diagnostic Kit and Diagnostic Method" is replaced with "sample containing a material produced during the production process of the processed product". The tester described in the above section "Tester" may also be used.

EXAMPLES

Examples of the present invention will be described below. The technical scope of the present invention is not limited by these Examples.

Example 1: Identification of Epitope

Epitope of ω-5 Gliadin
An epitope of ω-5 gliadin was identified by the following procedure.
(A) Epitope Mapping (1)
Epitope mapping was performed by using a library of overlapping peptides (15 amino acids in length) corresponding to the full-length amino acid sequence of ω-5 gliadin from bread wheat (SEQ ID NO: 51).
Each synthesized peptide was shifted by 10 amino acids. In other words, each peptide overlaps with the previous peptide and the next peptide, each by 5 amino acids.
Intavis CelluSpots™ technique was used for preparing a peptide array. Specifically, the peptide array was prepared by the following procedures: (1) synthesizing a target peptide on an amino-modified cellulose disk by using an automated synthesizer (MultiPep RS from Intavis), (2) dissolving said amino-modified cellulose disk to obtain a solution of a peptide bound to cellulose, and (3) spotting said peptide bound to cellulose on a coated slide glass. The detail of each procedure is as follows.
(1) Peptide Synthesis
Peptide synthesis was performed in a step-wise manner by using a 9-fluorenylmethoxycarbonyl (Fmoc) chemical reaction on the amino-modified cellulose disk in a 384-well plate for synthesis. Specifically, an amino acid with a Fmoc group attached to an amino group thereof was activated by a solution of N,N'-diisopropylcarbodiimide (DIC) and 1-hydroxybenzotriazole (HOBt) in dimethylformamide (DMF) and was dropped onto said cellulose disk, thereby allowing said amino acid with a Fmoc group attached thereto to bind to the amino group on the cellulose disk (coupling). After capping an unreacted amino group with acetic anhydride, the disk was washed with DMF, and furthermore treated with piperidine and washed with DMF, thereby removing the Fmoc group from the amino group of the amino acid bound to the amino group on the cellulose disk. Peptide synthesis was performed by repeatedly performing the above-mentioned coupling, capping, and removal of the Fmoc group on said amino acid bound to the amino group on the cellulose disk, thereby extending the amino terminus.
(2) Dissolution of Amino-Modified Cellulose Disk
The cellulose disk with a target peptide bound thereto that was obtained from the above "(1) Peptide Synthesis" was transferred into a 96-well plate. For deprotecting a side chain of the amino acid, the disk was treated with a mixed solution for deprotection of the side chain, the mixed solution containing trifluoroacetic acid (TFA), dichloromethane, triisopropylsilane (TIPS), and water. Subsequently, the deprotected peptide bound to cellulose was dissolved in a mixed solution of TFA, perfluoromethanesulfonic acid (TFMSA), TIPS, and water, precipitated with tetrabutyl methyl ether (TBME), resuspended in dimethylsulphoxide (DMSO), and mixed with a mixed solution of NaCl, sodium citrate, and water, thereby obtaining a peptide solution for slide spotting.
(3) Spotting of Solution of Peptide Bound to Cellulose
The peptide solution for slide spotting obtained in the above "(2) Dissolution of Amino-modified Cellulose Disk" was spotted on an Intavis CelluSpots™ slide by using an Intavis slide spotting robot and this was dried to prepare a peptide array.
Said peptide array was used to measure whether each peptide fragment is bound by an IgE antibody in the serum from a WDEIA patient due to an antigen-antibody reaction, or not. This measurement was performed in accordance with the following procedures.
(1) The peptide was shaken in PBST solution (PBS buffer containing 0.1% Tween 20 as a nonionic surfactant) with 5% skimmed milk for one hour at room temperature.
(2) The array was shaken in PBST solution with 2% serum and 5% skimmed milk for one hour at room temperature.
(3) The array was washed with PBST solution for 5 minutes (three times).
(4) An anti-human IgE antibody-HRP (1:10,000, PBST solution with 5% skimmed milk) was added and the array was shaken for one hour at room temperature.
(5) The array was washed with PBST solution for 5 minutes (three times).
(6) Pierce ECL Plus Western Blotting Substrate (manufactured by Thermo Fisher Scientific) was added and shaken for 5 minutes at room temperature.
(7) Chemiluminescence of the peptide that was treated as described in the above (1) to (6) was measured by using Amersham Imager 600.
Consequently, it was confirmed that the IgE antibody bound, in a manner specific to a patient, to a peptide of spot No. 1 (SEQ ID NO: 6) and a peptide of spot No. 2 (SEQ ID NO: 13), the peptides comprising no known epitope (FIG. 1). These peptides corresponded to amino acids 221 to 235 and 161 to 175 of the full-length amino acid sequence of ω-5 gliadin from bread wheat (SEQ ID NO: 51), respectively.
(B) Epitope Mapping (2): Overlapping
Based on the sequences (SEQ ID NOs: 6 and 13) of the peptides to which the IgE antibody in the serum bound in a manner specific to a patient in the above (A), a library of overlapping peptide fragments (10 amino acids in length) was prepared. The library was prepared using the sequences where sequences of the previous sequence and the next sequence of the aforementioned peptides in the full-length amino acid sequence of ω-5 gliadin from bread wheat (SEQ ID NO: 51) were added to the aforementioned peptides, and epitope mapping was performed.

Each synthesized peptide was shifted by one amino acid. In other words, each peptide overlaps with the previous peptide and the next peptide, each by 9 amino acids.

The library was prepared by the following procedures. Specifically, the library was prepared by (1) synthesizing a target peptide on an amino-modified resin with the automated synthesizer (MultiPep RS from Intavis) and (2) eluting the peptide from said amino-modified resin. The detail of each procedure is as follows.

(1) Peptide Synthesis

The target peptide was synthesized on the amino-modified resin in a 96-well plate by a method similar to that described above for (A). Biotin was bound to the amino terminus of the synthesized target peptide, with the biotin and the peptide sandwiching amino caproic acid derived from Fmoc-Acp (6)-OH as a spacer.

(2) Elution of Peptide from Amino-Modified Resin

Said amino-modified resin to which the obtained target peptide was bound was treated with a mixed solution of TFA, TIPS, and water, thereby eluting the peptide from said amino-modified resin. Then, the peptide was precipitated with TBME to obtain the target peptide and prepare the library.

Said library was used to measure whether each peptide fragment is bound by the IgE antibody in the serum from a patient due to an antigen-antibody reaction, or not, and identify a sequence common to the peptides bound by the IgE antibody from the patient, thereby determining a peptide having the shortest amino acid sequence that serves as an epitope. Measurement was performed by an ELISA method in accordance with the following procedures.

(1) 10 μg/ml biotin-bound peptide of the library was prepared in PBST solution and was shaken in an avidin-coated ELISA plate for one hour at room temperature.

(2) The plate was washed with PBST solution.

(3) The plate was shaken in PBST solution with 1% skimmed milk for one hour at room temperature.

(4) The plate was shaken in PBST solution with 2% serum and 1% skimmed milk for one hour at room temperature.

(5) The plate was washed with PBST solution.

(6) Anti-human IgE antibody-HRP (1:10,000, PBST solution with 1% skimmed milk) was added and the plate was shaken for one hour at room temperature.

(7) The plate was washed with PBST solution.

(8) 20 μl of TMB ELISA (manufactured by Thermo Fisher Scientific) was added and the plate was shaken for 15 minutes at room temperature.

(9) 20 μl of 2 M sulfuric acid was added to quench an enzymatic reaction.

(10) An absorbance at 450 nm was measured.

QFPQQQFPQQEFPQQQQFPQQQIAR (SEQ ID NO: 15), a subsequence of ω-5 gliadin from bread wheat, was measured by the overlapping technique in the library prepared based on SEQ ID NO: 6 and the obtained result is shown in FIG. 2. QFLQQQQFPQQQPPQQHQFPQQQL (SEQ ID NO: 23), a subsequence of ω-5 gliadin from bread wheat, was measured by the overlapping technique in the library prepared based on SEQ ID NO: 13 and the obtained result is shown in FIG. 2. The horizontal axis in each figure shows absorbance.

For SEQ ID NO: 15, the result showed that strong binding between the polypeptides having an amino acid sequence of SEQ ID NOs: 18 and 20, particularly SEQ ID NO: 20 and the IgE antibody from the patient was observed. For SEQ ID NOs: 17 and 19, slightly weaker binding with the IgE antibody from the patient was observed. For SEQ ID NOs: 16 and 21, no binding with the IgE antibody from the patient was observed. Therefore, SEQ ID NO: 22, which is a sequence common to SEQ ID NOs: 17 to 20, was identified to be the shortest amino acid sequence to serve as the epitope (FIG. 2).

For SEQ ID NO: 23, strong binding between polypeptides having an amino acid sequence of SEQ ID NOs: 25 and 26, particularly SEQ ID NO: 26 and the IgE antibody from the patient was observed. For SEQ ID NO: 27, slightly weaker binding with the IgE antibody from the patient was observed. For SEQ ID NOs: 24 and 28, no binding with the IgE antibody from the patient was observed. Therefore, SEQ ID NO: 29, which is a sequence common to SEQ ID NOs: 25 to 27, was identified to be the shortest amino acid sequence to serve as the epitope (FIG. 2).

On the other hand, although the amino acid sequences of SEQ ID NOs: 43 to 45 shown in FIG. 2 are already known epitopes of ω-5 gliadin (Non Patent Literature 1), they showed poor reactivity with the IgE antibody from the patient in this test.

(C) Epitope Mapping (3): Alanine Scanning

The amino acid sequence of SEQ ID NO: 22 and the amino acid sequence of SEQ ID NO: 29 identified in the above-mentioned (B) were subjected to a technique referred to as alanine scanning (Non Patent Literature 1). Specifically, a library of peptide fragments was prepared by a technique similar to that described above in (B), in which the peptide fragments were produced by substituting one amino acid at a time with alanine in each amino acid sequence of SEQ ID NO: 6 and SEQ ID NO: 13, starting from the amino acid at an amino terminal side. Then, a technique similar to that described above in (B) was used to measure whether each peptide fragment was bound by the IgE antibody in the serum from a patient and a healthy subject, or not. When alanine substitution of an amino acid at a certain position led to loss or reduction of binding activity to the IgE antibody from the patient and development of binding activity to the IgE antibody from the healthy subject, the amino acid was determined to be an amino acid important for expression of inherent antigenicity or an amino acid affecting expression of inherent antigenicity. When alanine substitution of an amino acid at a certain position led to retained binding activity to the IgE antibody from the patient and did not lead to development of binding activity to the IgE antibody from the healthy subject, the amino acid was determined to be an amino acid not important for expression of inherent antigenicity and substitutable. A common sequence important for expression of inherent antigenicity was discovered by this analysis.

Figure 3:
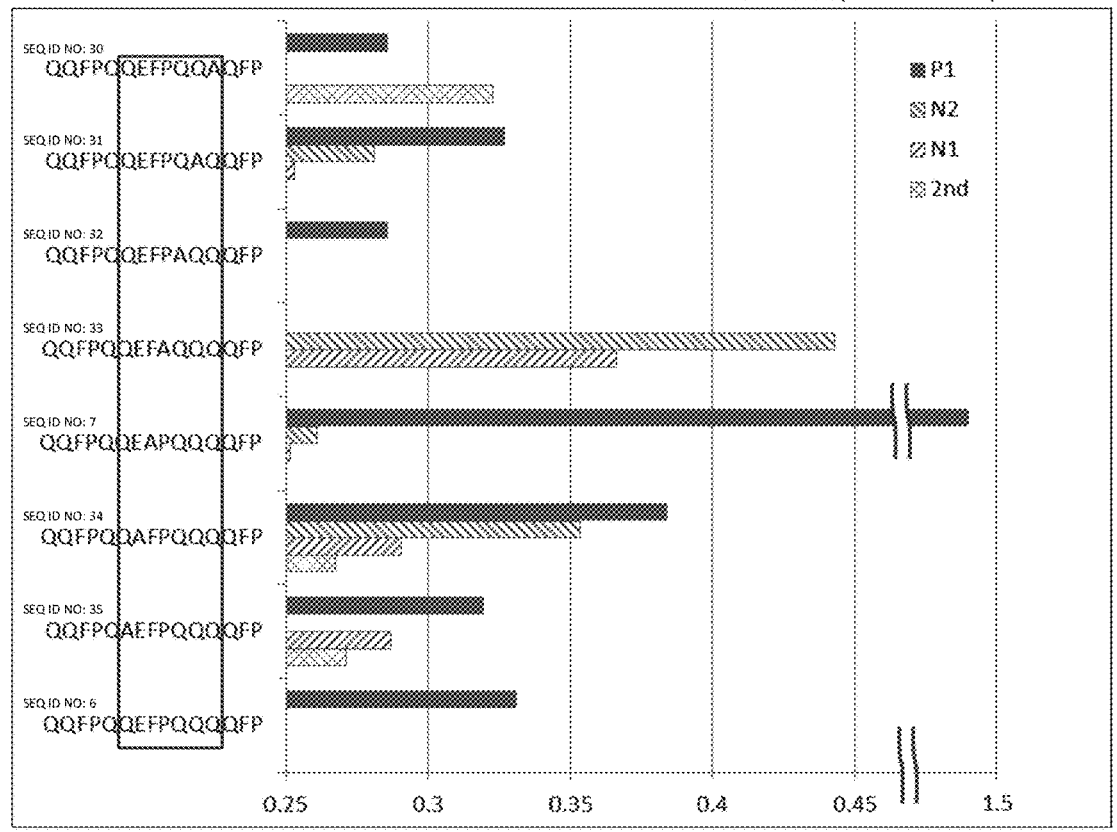
FIG. 3 is a diagram showing the result of investigation of positions important for exerting antigenicity in SEQ ID NOs: 22 and 29 by an alanine scanning technique. The number on the horizontal axis denotes a value of coloration intensity at 450 nm measured by an absorption spectrometer (Abs.). In this figure, a double wavy line denotes that a value is not shown, P1 denotes that the serum from patient 1 was used, N1 and N2 denote that the sera from healthy individuals 1 and 2 were used, and 2nd denotes that an anti-human IgE antibody as a secondary antibody was used alone.
Figure 3:
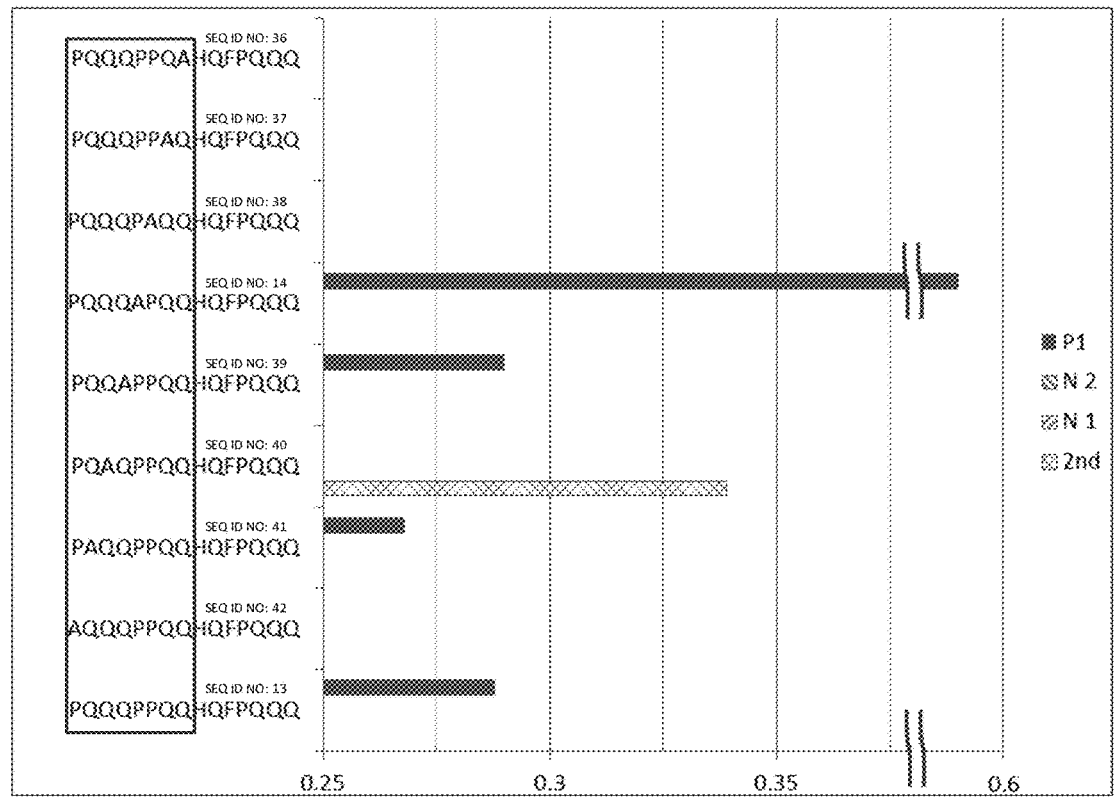

The result of alanine scanning performed on the amino acid sequence of SEQ ID NO: 22 and the result of alanine scanning performed on the amino acid sequence of SEQ ID NO: 29 are shown in FIG. 3, respectively. The horizontal axis in each figure shows absorbance.

The result for SEQ ID NO: 22 showed that binding activity to the IgE antibody from the patient was lost or reduced in SEQ ID NOs: 33 and 30, in which amino acids at positions 4 and 7 in SEQ ID NO: 22 were substituted with alanine, respectively. SEQ ID NO: 33 further developed binding activity to the IgE antibody from the healthy subject and SEQ ID NO: 30 further developed binding activity to an anti-human IgE antibody as a secondary antibody. SEQ ID NO: 34, in which an amino acid at position 2 was substituted with alanine showed slightly increased binding activity to the IgE antibody from the patient but developed binding activity to the IgE antibody from the healthy subject. Consequently, these amino acids at positions 2, 4, and 7 were found to be amino acids particularly important for expression of inherent antigenicity. SEQ ID NOs: 35 and 31, in which amino acids at positions 1 and 6 were substituted with alanine, respectively, showed slightly reduced binding activity to the IgE antibody from the patient but developed a relatively low level of binding activity to the IgE antibody from the healthy subject and the anti-human IgE antibody as the secondary antibody. Therefore, it was determined that these amino acids were amino acids that affect expression of inherent antigenicity. SEQ ID NO: 7, in which an amino acid at position 3 was substituted with alanine, retained binding activity to the IgE antibody from the patient and developed little binding activity to the IgE antibody from the healthy subject and the anti-human IgE antibody as the secondary antibody. SEQ ID NO: 32, in which an amino acid at position 5 was substituted with alanine, showed reduced binding activity to the IgE antibody from the patient but did not develop binding activity to the IgE antibody from the healthy subject or the anti-human IgE antibody as the secondary antibody. Therefore, it was concluded that these amino acids at positions 3 and 5 were substitutable amino acids. More remarkably, SEQ ID NO: 7 showed substantially increased binding activity to the IgE antibody from the patient (FIG. 3).

For SEQ ID NO: 29, SEQ ID NOs: 42, 40, and 38 to 36, in which amino acids at positions 1, 3, and 6 to 8 were substituted with alanine, respectively, showed loss of binding activity to the IgE antibody from the patient and thus, these amino acids were found to be amino acids particularly important for expression of inherent antigenicity. SEQ ID NO: 40 further developed binding activity to the anti-human IgE antibody as the secondary antibody. SEQ ID NO: 41, in which an amino acid at position 2 was substituted with alanine, showed a relatively low level of reduction of binding activity to the IgE antibody from the patient, and thus, it was concluded that this amino acid was an amino acid that affect expression of inherent antigenicity. SEQ ID NOs: 39 and 14, in which amino acids at positions 4 and 5 were substituted with alanine, respectively, retained binding activity to the IgE antibody from the patient and did not develop binding activity to the IgE antibody from the healthy subject, and thus, it was concluded that these amino acids were substitutable amino acids. More remarkably, SEQ ID NO: 14 showed substantially increased binding activity to the IgE antibody from the patient (FIG. 3).

Example 2: Investigation of Cross-Reactivity Based on Amino Acid Sequence

Amino acids important for binding activity to the IgE antibody from the patient were identified in polypeptides of SEQ ID NOs: 6 and 13 in the above (C) and SEQ ID NOs: 1 and 8 (hereinafter may be referred to as a key sequence) were obtained from SEQ ID NOs: 6 and 13, respectively. SEQ ID NO: 6 and SEQ ID NO: 13 were used as a query sequence and SEQ ID NO: 1 and SEQ ID NO: 8 as a key sequence were used as a PHI pattern sequence for SEQ ID NO: 6 and SEQ ID NO: 13, respectively. Cross-reactivity was investigated based on an amino acid sequence by PHI-BLAST analysis with default parameters of PHI-BLAST.

It followed that when SEQ ID NO: 6 was used as the query sequence and SEQ ID NO: 1 as the key sequence was used as the PHI pattern sequence, the following proteins had hits: proteins from a plant of Poaceae such as bread wheat and einkorn wheat; a plant of Brassicaceae such as a colza and a radish; a plant of Rosaceae such as a sweet cherry and a peach; a plant of Caricaceae such as a *papaya*; a plant of Leguminosae such as a pigeon pea and a soybean; a plant of Vitaceae such as an European grape; a plant of Juglandaceae such as a Shinano walnut; a plant of Euphorbiaceae such as a cassava and a *hevea*; a plant of Amaranthaceae such as a *quinoa* and spinach; a plant of Bromeliaceae such as a pineapple; a plant of Solanaceae such as a potato; a plant of Asparagaceae such as an *asparagus*; a plant of Cucurbitaceae such as a melon; a plant of Rutaceae such as an orange and a clementine; a plant of Cupressaceae such as a Japanese cedar; a plant of Betulaceae such as a Japanese white birch; and a fungus such as *Aspergillus turcosus*. This result shows that SEQ ID NO: 1 can be used for detecting cross-reactivity of an antigen not only across species but also beyond a genus or even a plant kingdom.

When SEQ ID NO: 13 was used as the query sequence and SEQ ID NO: 8 as the key sequence was used as the PHI pattern sequence, as described above, proteins from the plant of Poaceae, the plant of Brassicaceae, the plant of Rosaceae, the plant of Caricaceae, the plant of Leguminosae, the plant of Vitaceae, the plant of Juglandaceae, the plant of Euphorbiaceae, the plant of Amaranthaceae, the plant of Bromeliaceae, the plant of Solanaceae, the plant of Asparagaceae, the plant of Cucurbitaceae, the plant of Rutaceae, the plant of Cupressaceae, the plant of Betulaceae, the fungus, and the like had hits. This result shows that SEQ ID NO: 8 can be used for detecting cross-reactivity of an antigen across species as well as beyond genus.

The invention claimed is:

1. A polypeptide that specifically binds to an IgE antibody from an allergic patient, wherein the patient is allergic to ω-5 gliadin or a composition having IgE cross reactivity to ω-5 gliadin, wherein the polypeptide consists of an amino acid sequence selected from the group consisting of SEQ ID NOs: 11, 12 and 25, and wherein said polypeptide is immobilized to a carrier or a surface.

2. A kit for diagnosing allergy, the kit comprising at least one polypeptide according to claim 1.

3. A composition for diagnosing allergy, the composition comprising, as an antigen, at least one polypeptide according to claim 1.

4. A method for diagnosing allergy to ω-5 gliadin or a composition having IgE cross reactivity to ω-5 gliadin in a subject, the method comprising detecting binding between an antigen and an IgE antibody in a sample from the subject, wherein the antigen is at least one polypeptide that specifically binds to IgE antibody from an allergic patient, wherein the allergic patient is allergic to ω-5 gliadin or a composition having IgE cross reactivity to ω-5 gliadin, wherein the polypeptide consists of an amino acid sequence selected from the group consisting of SEQ ID NOs: 11, 12 and 25, and wherein binding between the IgE antibody and the antigen is indicative that the subject is allergic to ω-5 gliadin or the composition having IgE cross reactivity to ω-5 gliadin.

5. A pharmaceutical composition comprising at least one polypeptide according to claim 1.

6. The pharmaceutical composition according to claim 5, wherein the pharmaceutical composition is formulated for the treatment of allergy.

7. A method for treating allergy to ω-5 gliadin or a composition having IgE cross reactivity to ω-5 gliadin, the method comprising administering an amount of at least one polypeptide to a patient in need of treatment of said allergy to induce hyposensitization, wherein the polypeptide specifically binds to an IgE antibody from an allergic patient and consists of an amino acid sequence selected from the group consisting of SEQ ID NOs: 11, 12 and 25; and wherein the patient is allergic to ω-5 gliadin or a composition having IgE cross reactivity to ω-5 gliadin.

8. A method for diagnosing a patient having allergy to ω-5 gliadin or a composition having IgE cross reactivity to ω-5 gliadin, the method comprising:
  (i) administering at least one polypeptide to the patient;
  (ii) monitoring reaction of the patient; and
  (iii) determining that the patient is allergic to ω-5 gliadin or the composition having IgE cross reactivity to ω-5 gliadin, when the patient shows a reaction;
wherein the polypeptide specifically binds to an IgE antibody from a subject allergic to ω-5 gliadin or the composition having IgE cross reactivity to ω-5 gliadin, said polypeptide consisting of an amino acid sequence selected from the group consisting of SEQ ID NOs: 11, 12 and 25.

9. The polypeptide of claim 1, wherein the carrier or the surface is suitable for detecting binding between said IgE antibody and said polypeptide through immunoassay.

* * * * *